(12) United States Patent
Schetz

(10) Patent No.: US 10,766,866 B2
(45) Date of Patent: Sep. 8, 2020

(54) DETERRENTS FOR ARTHROPODS AND MARINE ORGANISMS

(71) Applicant: University of North Texas Health Science Center at Fort Worth, Fort Worth, TX (US)

(72) Inventor: John A. Schetz, Fort Worth, TX (US)

(73) Assignee: University of North Texas Health Science Center at Fort Worth, Fort Worth, TX (US)

(*) Notice: Subject to any disclaimer, the term of this patent is extended or adjusted under 35 U.S.C. 154(b) by 0 days.

(21) Appl. No.: 16/175,568

(22) Filed: Oct. 30, 2018

(65) Prior Publication Data
US 2019/0292156 A1    Sep. 26, 2019

Related U.S. Application Data

(60) Provisional application No. 62/578,987, filed on Oct. 30, 2017.

(51) Int. Cl.
| | | |
|---|---|---|
| *C07D 233/64* | (2006.01) |
| *A01N 33/10* | (2006.01) |
| *A01N 43/50* | (2006.01) |
| *C07C 225/10* | (2006.01) |
| *A61K 31/135* | (2006.01) |
| *A61K 31/506* | (2006.01) |
| *A61K 31/137* | (2006.01) |
| *A61K 31/4164* | (2006.01) |
| *A61K 45/06* | (2006.01) |
| *A61P 35/00* | (2006.01) |
| *A61K 31/4174* | (2006.01) |

(52) U.S. Cl.
CPC ............ *C07D 233/64* (2013.01); *A01N 33/10* (2013.01); *A01N 43/50* (2013.01); *A61K 31/135* (2013.01); *A61K 31/137* (2013.01); *A61K 31/4164* (2013.01); *A61K 31/4174* (2013.01); *A61K 31/506* (2013.01); *A61K 45/06* (2013.01); *A61P 35/00* (2018.01); *C07C 225/10* (2013.01)

(58) Field of Classification Search
CPC .............................. C07D 233/64; A01N 33/10
See application file for complete search history.

(56) References Cited

U.S. PATENT DOCUMENTS

| | | |
|---|---|---|
| 2006/0020013 A1 | 1/2006 | Huber et al. |
| 2007/0167506 A1 | 7/2007 | Chubb et al. |
| 2016/0280668 A1 | 9/2016 | Hallenbach et al. |

FOREIGN PATENT DOCUMENTS

WO    2015011178 A1    1/2015

OTHER PUBLICATIONS

International Search Report and Written Opinion for PCT/US2018/58263 dated Feb. 22, 2019, 12 pages.
Sharma, et al. "An efficient one-pot synthesis of 2-benzylpyrroles and 3-benzylindoles", Applied Organometallic Chemistry, vol. 25, pp. 305-309, Jan. 10, 2011.
Pubmed Compound Summary for CID 11768828, "3-Benzyl-1H-pyrrole", U.S. National Library of Medicine, p. 1-14, Oct. 26, 2006 (https://pubchem.ncbi.nlm.nih.gov/compound/11768828).
Galley, et al. "Optimisation of imidazole compounds as selective TAAR1 agonists: Discovery of RO5073012", Bioorganic & Medicinal Chemistry Letters, vol. 22, pp. 5244-5248, Jun. 23, 2012.
Wang, et al. "Liquid-Phase Traceless Synthesis of 3,5-Disubstituted 1,2,4-Triazoles", Synlett, vol. 17, pp. 2595-2598, 2005.

*Primary Examiner* — Golam M Shameem
(74) *Attorney, Agent, or Firm* — Polsinelli PC

(57) ABSTRACT

The present invention related to compounds, compositions, methods of use, and processes for preparing compound which are useful as deterrents for terrestrial arthropods and marine organisms.

22 Claims, 12 Drawing Sheets

AZ1399

Calculated Boiling Point Estimate = 406°C

| | Affinity (nM ± SEM) | |
|---|---|---|
| | Hsα$_{2A}$-AR | Hsα$_{2C}$-AR |
| | 3205 ± 672 | 2106 ± 385 |

| Potency (EC$_{50}$, nM ± SEM) | | Selectivity (Fold-Change) K$_{i(Hsα2C-AR)}$/EC$_{50(OctR)}$ |
|---|---|---|
| 367 ± 237 | DmOctR | 8.7 / 5.7 |
| 82 ± 25 | PaOctR | 39 / 26 |
| -- | AeOctR | -- / -- |
| 11 ± 3.7 | AgAOctR | 291 / 191 |
| -- | AgBOctR | -- / -- |
| 43 ± 11 | IsTOctR | 75 / 49 |

Calculated Boiling Point Estimate = 398°C

| | | Affinity (nM ± SEM) | |
|---|---|---|---|
| | | 1314 ± 247 Hsα$_{2A}$-AR | 973 ± 146 Hsα$_{2C}$-AR |
| | | Selectivity (Fold-Change) $K_{i(Hsα2C-AR)}/EC_{50(OctR)}$ | |
| Potency (EC$_{50}$, nM ± SEM) | DmOctR | 1.5 | 1.2 |
| | PaOctR | 25 | 11 |
| | AeOctR | 0.066 | 0.049 |
| | AgAOctR | 571 | 423 |
| | AgBOctR | -- | -- |
| | IsTOctR | 38 | 28 |

Potency (EC$_{50}$, nM ± SEM):
- DmOctR: 846 ± 440
- PaOctR: 85 ± 34
- AeOctR: > 20,000
- AgAOctR: 2.3 ± 0.69
- AgBOctR: --
- IsTOctR: 35 ± 7.4

Calculated Boiling Point Estimate = 389°C

| | | Affinity (nM ± SEM) | |
|---|---|---|---|
| | | $Hsα_{2A}$-AR | $Hsα_{2C}$-AR |
| | | 109 ± 16 | 231 ± 46 |
| | | Selectivity (Fold-Change) $K_{i(Hsα_{2C}\text{-AR})}/EC_{50(OctR)}$ | |
| Potency ($EC_{50}$, nM ± SEM) | DmOctR | 8.7 ± 2.7 | 13 | 27 |
| | PaOctR | 0.44 ± 0.23 | 247 | 525 |
| | AeOctR | 12 ± 3.2 | 9 | 19 |
| | AgAOctR | 0.013 ± 0.0046 | 8385 | 17769 |
| | AgBOctR | -- | -- | -- |
| | IsTOctR | 0.51 ± 0.28 | 214 | 453 |

FIG. 6

| Value ± SEM | AZ1409 Z-isomer | AZ1440 E-isomer | AZ1409 Z-isomer | AZ1409 E-isomer |
|---|---|---|---|---|
| Potency (nM) | 58 ± 41 | 10 ± 4.7 | 969 ± 358 | 90 ± 25 |
| Efficacy (α) | 0.97 ± 0.084 | 1.01 ± 5.45 | 0.75 ± 0.056 | 0.43 ± 0.016 |

FIG. 11

| Value ± SEM | AK128046 | CN19745 | AK128046 | CN19745 |
|---|---|---|---|---|
| Potency (nM) | 65 ± 22 | 120 ± 49 | 3135 ± 917 | 1657 ± 1403 |
| Efficacy (α) | 0.98 ± 0.043 | 0.94 ± 0.050 | 0.78 ± 0.062 | 0.39 ± 0.052 |
| Selectivity over h$α_{2C}$-AR (fold) | 163 | 88 | 3 | 6 |

FIG. 12

DETERRENTS FOR ARTHROPODS AND MARINE ORGANISMS

CROSS REFERENCE TO RELATED APPLICATIONS

The present application claims benefit under 35 U.S.C. § 119 of U.S. Provisional Patent Application No. 62/578,987, entitled, "DETERRENTS FOR ARTHROPODS AND MARINE ORGANISMS" filed Oct. 30, 2017, the entirety of which is incorporated herein by reference.

FIELD OF THE INVENTION

The present disclosure generally relates to deterrents of terrestrial arthropods, marine arthropods, and other aquatic and marine organisms.

BACKGROUND OF THE INVENTION

Aquatic and marine biofouling is the attachment of organisms to wetted or submerged man-made surfaces. Specifically, the accumulation of these biofouling organisms poses many significant problems. As one example, accumulation of barnacles or mussels on ship hulls reduces the ship performance by increasing hydrodynamic drag which reduces maneuverability and increases fuel consumption. Another example, the accumulation of zebra mussels leads to clogging of water supply pipes, water intakes, and heat exchangers which restricts water flow in these structures resulting in a reduction or loss of performance for facilities that utilizing the water. As a further example, navigational buoys can sink under the weight of the attached biofouling organisms, and dock pilings and ship hulls can deteriorate faster through the corrosion of steel and concrete. Many treatments have been developed to counteract biofouling which include specialized coatings, including fouling release coatings and biocide-impregnated coatings. But, these above methods have limitations such as bioaccumulation of released toxic antifouling substances or restrictions or limits to their performance.

Insects such as mosquitos, lice, flies, fleas, and ticks are known to be vectors for the transmission of infectious agents such as parasites, viruses, and bacteria. Some of the diseases which can be transmitted by these insects include malaria, Dengue fever, Yellow fever, Zika virus, Chikungunya, Lyme disease, West Nile virus, and others. In some parts of the world, these diseases have become a public health issue. In response, various types of insect repellents have been developed to repel insects from landing and biting a host. Commercial compounds such as DEET (N,N-diethyl-meta-toluamide) have been shown to be effective repellents, and relatively safe when used as directed. However, most people do not use DEET as directed and there is also significant consumer aversion to DEET. Aside from limitations to its application such as avoiding contact with eyes, open skin, and mucosal membranes, there are a number of drawbacks to DEET including that it is structurally similar to toluene and thus dissolves many types of paints, coatings and textiles and there are concerns of resistance because it must be used at concentrations that affect target organism fitness.

Octopamine receptors (OctR) belong to the biogenic amine receptor family which includes receptors for dopamine, serotonin, and tyramine. Octopamine is a major signaling molecule in arthropods, including insects and barnacle cyprids, with neuromodulator, neurotransmitter, and neurohormone functions. Octopamine receptors can be subdivided into at least two different subclasses called alpha-like ($\alpha$-like) and beta-like ($\beta$-like) OctRs. We found that molecules which activate ($\alpha$-like OctR) would disrupt the biting activities of insects and the settlement activity of barnacle cyprids. In the past, small molecules have been developed to activate the OctRs; however these molecules also activate vertebrate alpha-2 adrenergic receptors ($\alpha_2$AR) homologues meaning that the molecules developed do not readily discriminate between invertebrates OctRs and vertebrate $\alpha_2$ARs. The interaction of these small compounds with vertebrate $\alpha_2$ARs produces sedative, tranquilizing, and muscle relaxation properties. Therefore, it has not been possible to find a highly selective small molecule that is capable of readily discriminating between arthropod OctR and vertebrate $\alpha_2$AR, thereby, deterring the arthropod while not also significantly affecting the host.

What is needed is a deterrent for arthropods and marine organisms which would be considered highly effective yet safe for vertebrates due to its high selectivity for a target invertebrate OctR over the off-target vertebrate $\alpha_2$AR.

SUMMARY OF THE INVENTION

Provided herein are compounds, compositions, methods for using these compositions, and processes for preparing these compounds which are useful as deterrents for terrestrial arthropod and aquatic and marine organisms.

In one aspect, disclosed herein are compounds comprising Formula (I) or salts thereof:

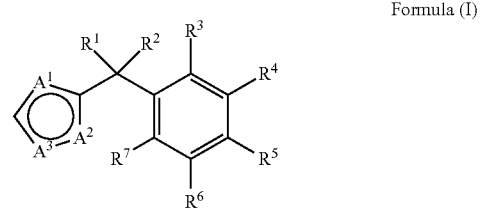

Formula (I)

wherein:

$A^1$, $A^2$, and $A^3$ is independently selected from a group consisting of carbon, nitrogen, oxygen, and sulfur;

$R^1$ and $R^2$ are independently selected from a group consisting of hydrogen, deuterium, hydroxyl, $C_1$-$C_6$ substituted or unsubstituted alkyl, $C_2$-$C_6$ substituted or unsubstituted alkenyl, $C_1$-$C_6$ substituted or unsubstituted alkoxy; or $R^1$ and $R^2$ may be taken together to form a $C_1$-$C_6$ substituted or unsubstituted alkenyl, or =O; and $R^3$, $R^4$, $R^5$, $R^6$, and $R^7$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, $R^1$ and $R^3$ may be taken together to form a $C_1$-$C_6$ substituted or unsubstituted cycloalkyl, or $C_2$-$C_6$ substituted or unsubstituted cycloalkenyl, $R^2$ and $R^3$ may be taken together to form a $C_1$-$C_6$ substituted or unsubstituted cycloalkyl, or $C_2$-$C_6$ substituted or unsubstituted cycloalkenyl, or $R^3$ and $R^4$ may be taken together to form a $C_1$-$C_6$ substituted or unsubstituted cycloalkyl, $C_2$-$C_6$ substituted or unsubstituted cycloalkenyl, or substituted or unsubstituted aryl.

In another aspect, disclosed herein are compositions comprising the compounds of Formula (I) or salts thereof, at least one additional component or "carrier", and optionally a known deterrent compound:

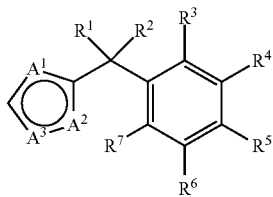

Formula (I)

wherein:

$A^1$, $A^2$, and $A^3$ is independently selected from a group consisting of carbon, nitrogen, oxygen, and sulfur;

$R^1$ and $R^2$ are independently selected from a group consisting of hydrogen, deuterium, hydroxyl, $C_1$-$C_6$ substituted or unsubstituted alkyl, $C_2$-$C_6$ substituted or unsubstituted alkenyl, $C_1$-$C_6$ substituted or unsubstituted alkoxy; or $R^1$ and $R^2$ may be taken together to form a $C_1$-$C_6$ substituted or unsubstituted alkenyl, or =O; and $R^3$, $R^4$, $R^5$, $R^6$, and $R^7$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, $R^1$ and $R^3$ may be taken together to form a $C_1$-$C_6$ substituted or unsubstituted cycloalkyl, or $C_2$-$C_6$ substituted or unsubstituted cycloalkenyl, $R^2$ and $R^3$ may be taken together to form a $C_1$-$C_6$ substituted or unsubstituted cycloalkyl, or $C_2$-$C_6$ substituted or unsubstituted cycloalkenyl, or $R^3$ and $R^4$ may be taken together to form a $C_1$-$C_5$ substituted or unsubstituted cycloalkyl, $C_2$-$C_6$ substituted or unsubstituted cycloalkenyl, or $C_2$-$C_6$ substituted or unsubstituted aryl.

In another aspect of the present disclosure encompasses methods of using the above composition comprising the compounds of Formula (I) or salts thereof, at least one additional component or "carrier", and optionally a known deterrent compound to deter marine biofouling organism.

In still another aspect of the present disclosure encompasses methods of using the above composition comprising the compounds of Formula (I) or salts thereof, at least one additional component or "carrier", and optionally a known deterrent compound to deter terrestrial arthropods.

In yet another aspect of the present disclosure encompasses processes for preparing compounds of Formula (Ia) or salts thereof. The process comprises contacting a compound of Formula (III) with a compound of Formula (IV) to form a compound of Formula (V). The process further comprises contacting a compound of Formula (V) with a compound of Formula (VI) to form a compound of Formula (Ia). The process for preparing the compound of Formula (I) is illustrated as follows:

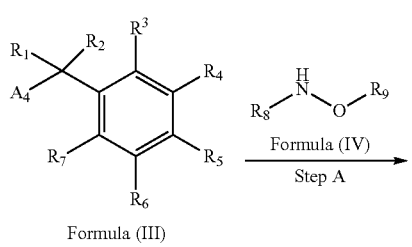

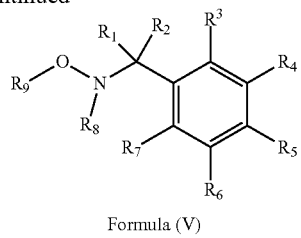

Formula (V)

Step B

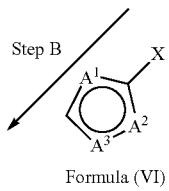

Formula (VI)

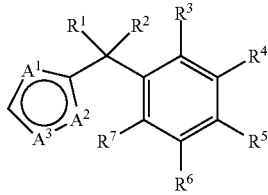

Formula (Ia)

wherein:

$A^1$, $A^2$, $A^3$, and $A^4$ are independently selected from a group consisting of C, N, O, and S;

$R^1$ and $R^2$ are taken together as =O;

$R^3$, $R^4$, $R^5$, $R^6$, and $R^7$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, or $R^3$ and $R^4$ may be taken together to form a $C_1$-$C_5$ substituted or unsubstituted cycloalkyl, $C_2$-$C_6$ substituted or unsubstituted cycloalkenyl; and $R^8$ and $R^9$ are independently selected from a group consisting of hydrogen, or $C_1$-$C_6$ substituted or unsubstituted alkyl; and X is a halogen.

In another aspect, disclosed herein are compounds comprising Formula (II) or salts thereof:

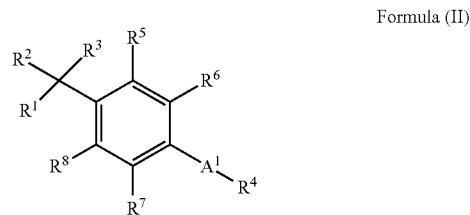

Formula (II)

wherein $A^1$ is selected from a group consisting of nitrogen, oxygen, and sulfur;

$R^1$, $R^2$, and $R^3$ are independently selected from a group is selected from a group consisting of hydrogen, hydroxyl, $C_1$-$C_6$ substituted or unsubstituted alkyl; $C_1$-$C_6$ substituted or unsubstituted alkenyl, $C_1$-$C_6$ substituted or unsubstituted alkoxy, or $R^1$ and $R^2$ may be taken together to form a $C_2$-$C_4$ substituted or unsubstituted alkenyl, or =O, and $R^4$, $R^5$, $R^6$, $R^7$, and $R^8$ each independently selected from a group comprising of hydrogen, halogen, $C_1$-$C_6$ alkyl, $C_1$-$C_6$ halogenated alkyl, or $C_1$-$C_6$ halogenated alkoxy.

In an additional aspect of the present disclosure encompasses compositions comprising the compounds of Formula (II) or salts thereof, at least one additional component or "carrier", and optionally a known deterrent compound:

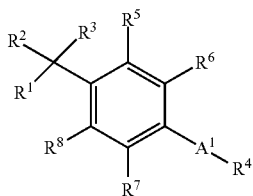

Formula (II)

wherein:

$A^1$, $A^2$, and $A^3$ is independently selected from a group consisting of carbon, nitrogen, oxygen, and sulfur;

$R^1$ and $R^2$ are independently selected from a group consisting of hydrogen, deuterium, hydroxyl, $C_1$-$C_6$ substituted or unsubstituted alkyl, $C_2$-$C_6$ substituted or unsubstituted alkenyl, $C_1$-$C_6$ substituted or unsubstituted alkoxy; or $R^1$ and $R^2$ may be taken together to form a $C_2$-$C_6$ substituted or unsubstituted alkenyl, or =O; and $R^3$, $R^4$, $R^5$, $R^6$, and $R^7$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, or $R^3$ and $R^4$ may be taken together to form a $C_1$-$C_5$ substituted or unsubstituted cycloalkyl, or $C_2$-$C_6$ substituted or unsubstituted cycloalkenyl.

In still another aspect of the present disclosure encompasses methods of using the above composition comprising the compounds of Formula (II) or salts thereof, at least one additional component or "carrier", and optionally a known deterrent compound to deter marine biofouling organisms.

In yet another aspect of the present disclosure encompasses methods of using the above composition comprising the compounds of Formula (II) or salts thereof, at least one additional component or "carrier", and optionally a known deterrent compound to deter terrestrial arthropods.

Other features and iterations of the invention are described in more detail below.

BRIEF DESCRIPTION OF THE FIGURES

The disclosure will be readily understood by the following detailed description in conjunction with the accompanying figures. The figures provide exemplary embodiments or aspects of the disclosure and do not limit the scope of the disclosure.

FIG. 3 shows the potency of AZ1399 tested against the octopamine receptors from *Balanus* (BiOctR), *Drosophila* (DmOctR), *Periplaneta* (PaOctR), *Anopheles* Form A (AgAOctR) and *Ixodes* (IsTOctR). AZ1399 is highly selective for the AgAOctR over *Homo sapien* $α_2$-AR subtypes.

FIG. 5 shows the potency of AZ1400 tested against the octopamine receptors from *Balanus* (BiOctR), *Drosophila* (DmOctR), *Periplaneta* (PaOctR), *Aedes* (AeOctR), *Anopheles* Form A (AgAOctR) and *Ixodes* (IsTOctR). AZ1400 is highly selective for the AgAOctR over *Homo sapien* $α_2$-AR subtypes.

FIG. 6 shows the potency of AZ0027 tested against the octopamine receptors from *Balanus* (BiOctR), *Drosophila* (DmOctR), *Periplaneta* (PaOctR), *Aedes* (AeOctR), *Anopheles* Form A (AgAOctR), *Balanus* (BiOctR) and *Ixodes* (IsTOctR). AZ0027 is highly selective for *Balanus barnacle*, *Periplaneta cockroach*, *Anopheles mosquito* and *Ixodes* tick OctRs over *Homo sapien* $α_2$-AR subtypes.

FIG. 11 compares the potency and efficacy of E- and Z-isomers of two tested compounds. The E-isomer of the ethylene-substituted compound (AZ1440) has higher potency than the Z-isomer (AZ1409) at the AgAOctR and both are full agonists, though at the IsTOctR both isomers have efficacies less than one making them partial agonists and the E-isomer is less efficacious than the Z-isomer FIG. 12 compares the potency and efficacy of compounds with a keto group as the bridge. AK128046 and CN19745 are full agonists with moderate potencies at *Anopheles* OctR, and high and moderate selectivity, respectfully over the human $α_{2c}$-AR.

DETAILED DESCRIPTION OF THE INVENTION

Figure 1A:
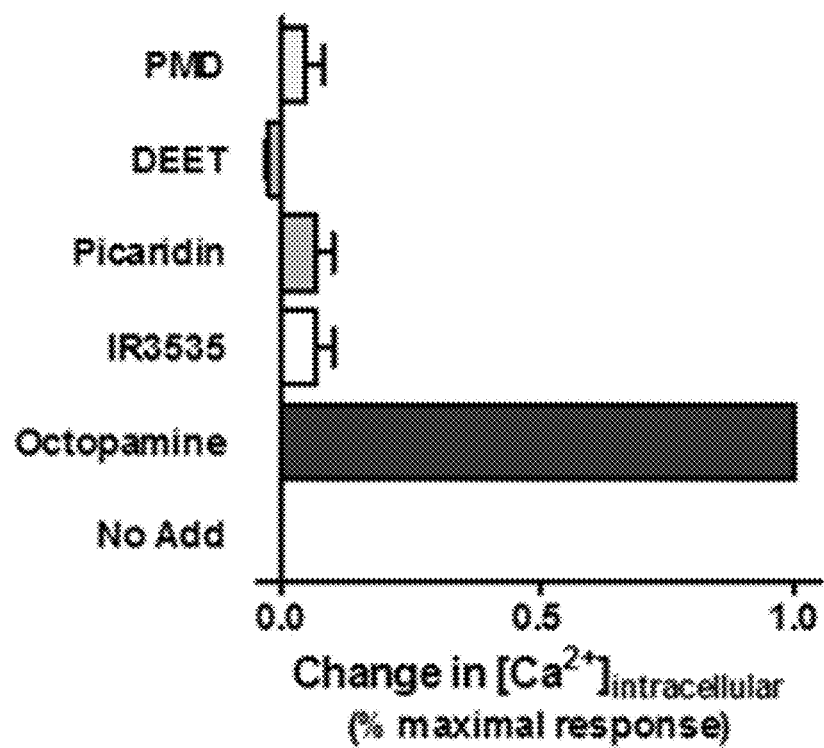
FIGS. 1A-1D show that commercial insect repellents have little or no detectable agonists activity at α-like OctRs as measured by a change in intercellular calcium concentration. The response of the commercial insect repellents is compared with a supersaturating concentration of the positive OctR endogenous agonist control octopamine. Specifically, we tested OctRs for *Drosophila melanogaster* (FIG. 1A), *Aedes aegypti* (FIG. 1B), *Ixodes scapularis* (FIG. 1C), and *Periplanta americana* (FIG. 1D), at an extremely high 100 µM concentration of the widely used insect repellents para-menthane-3,8-diol (PMD), N,N-diethyl-meta-toluamide (DEET), 1-(1-methylpropoxycarbonyl)-2-(2-hydroxyethyl)piperidine (picaridin), and ethyl butylacetylaminopropionate (IR3535). Note that while DEET, icaridin and IR3535 did not produce a significant agonist response at any of the OctRs tested, PMD produced significant agonist responses at the α-like OctR cloned from *Ixodes* and *Periplanta* and picardin produced significant agonist responses at the α-like OctR cloned from *Balanus*, but it required in each case an extremely high concentration (i.e., 100 µM) and the responses were as small compared to that for octopamine (FIG. 1C-1D).
Figure 1B:
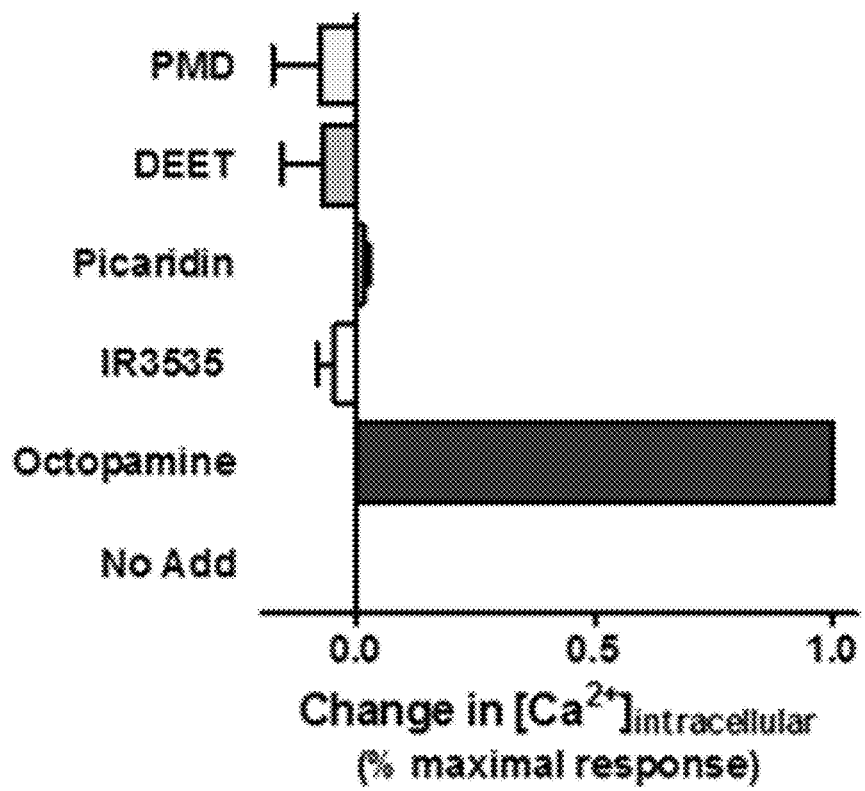
Figure 1C:
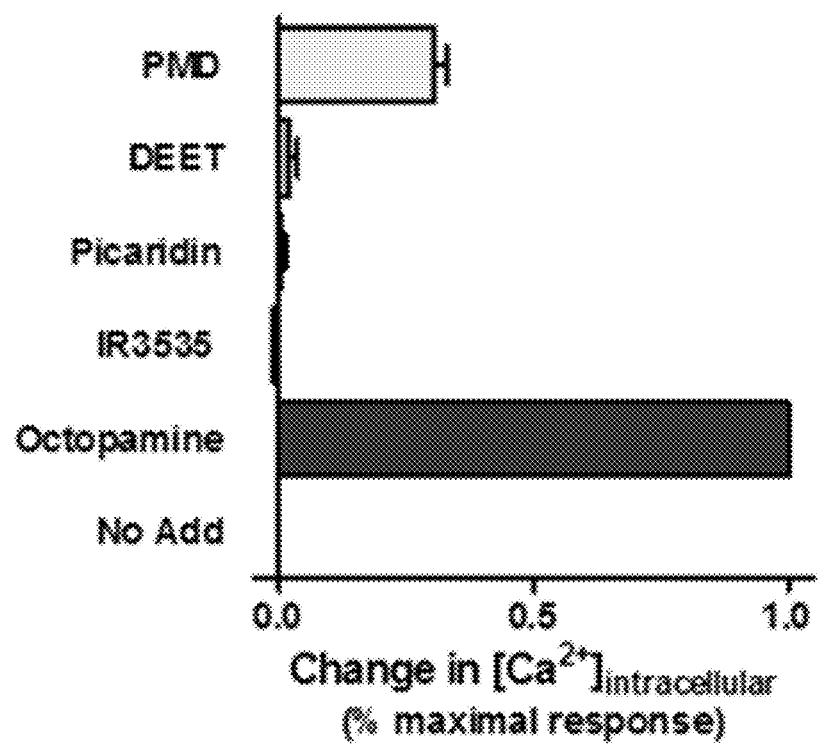
Figure 1D:
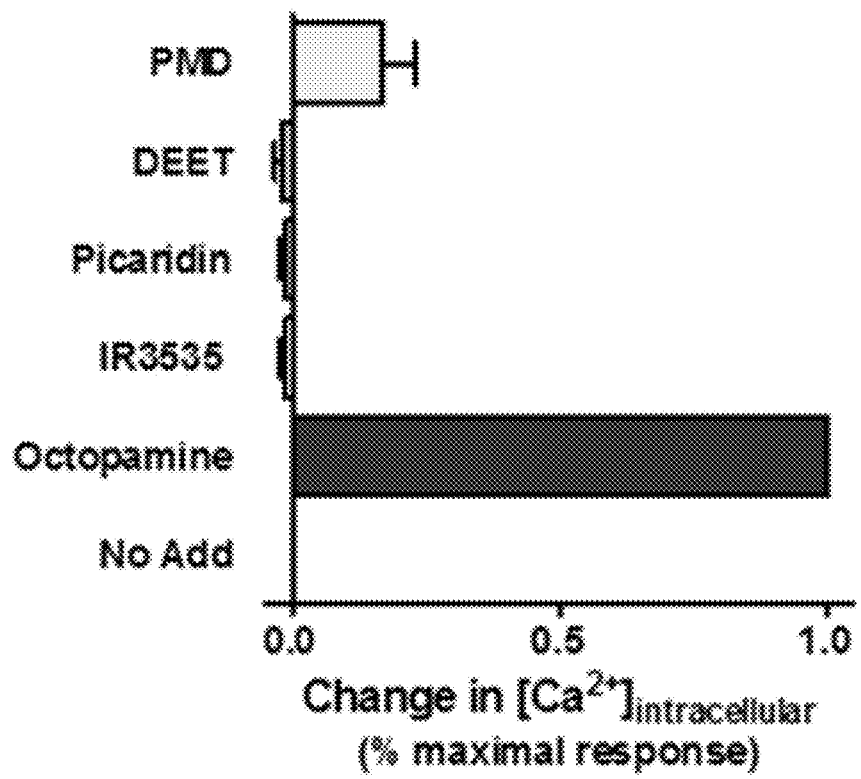

Disclosed herein are compounds useful as deterrents for terrestrial arthropods, marine arthropods, and aquatic and marine organisms, compositions which comprise these compounds, methods of use of these compositions, and methods of preparing these compounds.

These compounds and compositions have been shown to be highly effective against a wide variety of terrestrial arthropods, marine arthropods, and aquatic and marine organisms.

(I) Compounds Comprising Formula (I) and their Physical Properties

One aspect of the present disclosure encompasses compounds comprising Formula (I) or a salt thereof which may be useful as anthropod deterrents:

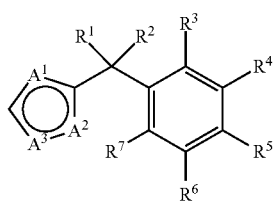

Formula (I)

wherein:

$A^1$, $A^2$, and $A^3$ is independently selected from a group consisting of carbon, nitrogen, oxygen, and sulfur;

$R^1$ and $R^2$ are independently selected from a group consisting of hydrogen, deuterium, hydroxyl, $C_1$-$C_6$ substituted or unsubstituted alkyl, $C_2$-$C_6$ substituted or unsubstituted alkenyl, $C_1$-$C_6$ substituted or unsubstituted alkoxy; or $R^1$ and $R^2$ may be taken together to form a $C_2$-$C_6$ substituted or unsubstituted alkenyl, or =O; and $R^3$, $R^4$, $R^5$, $R^6$, and $R^7$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, $R^1$ and $R^3$ may be taken together to form a $C_1$-$C_6$ substituted or unsubstituted cycloalkyl, or $C_2$-$C_6$ substituted or unsubstituted cycloalkenyl, $R^2$ and $R^3$ may be taken together to form a $C_1$-$C_6$ substituted or unsubstituted cycloalkyl, or $C_2$-$C_6$ substituted or unsubstituted cycloalkenyl, or $R^3$ and $R^4$ may be taken together to form a $C_1$-$C_5$ substituted or unsubstituted cycloalkyl, $C_2$-$C_6$ substituted or unsubstituted cycloalkenyl, or $C_2$-$C_6$ substituted or unsubstituted aryl.

In general, $A^1$, $A^2$, and $A^3$ are independently selected from a group consisting of carbon, nitrogen, oxygen, and sulfur. In an embodiment, $A^1$ is nitrogen, and $A^2$ and $A^3$ are carbon. In another embodiment, $A^3$ is nitrogen, and A1 and A3 are carbon. In an additional embodiment, $A^1$ and $A^2$ are nitrogen, and $A^3$ is carbon. In yet another embodiment, $A^1$ and $A^3$ are nitrogen, and $A^2$ is carbon. In still another embodiment, $A^1$, $A^2$, and $A^3$ are nitrogen.

Generally, $R^1$ and $R^2$ are independently selected from a group consisting of hydrogen, deuterium, hydroxyl, $C_1$-$C_6$ substituted or unsubstituted alkyl, $C_2$-$C_6$ substituted or unsubstituted alkenyl, $C_1$-$C_6$ substituted or unsubstituted alkoxy; or $R^1$ and $R^2$ may be taken together to form a $C_2$-$C_6$ substituted or unsubstituted alkenyl, or =O. In various embodiments, $R^1$ and $R^2$ are independently selected from a group consisting of hydrogen, deuterium, hydroxyl, $C_1$-$C_4$ substituted or unsubstituted alkyl, $C_2$-$C_4$ substituted or unsubstituted alkenyl, $C_1$-$C_4$ substituted or unsubstituted alkoxy; or $R^1$ and $R^2$ may be taken together to form a $C_2$-$C_4$ substituted or unsubstituted alkenyl, or =O. In some embodiments, $R^1$ and $R^2$ are independently selected from a group consisting of hydrogen, methyl, ethyl, propyl, isopropyl, methoxy, ethoxy, propoxy, isopropoxy, hydroxyl, —$CH_2CH=CH_2$, —$CH_2C(CH_3)=CH_2$, —$CH=C(CH_3)_2$, —$CH=CHCH_3$; or $R^1$ and $R^2$ may be taken together to form =$CH_2$, =$CHCH_3$, =$C(CH_3)_2$, or =O. In specific embodiments, $R^1$ and $R^2$ are independently selected from a group consisting hydrogen, methyl, methoxy, hydroxyl, —$CH_2CH=CH_2$, —$CH=CHCH_3$; or $R^1$ and $R^2$ may be taken together to form =$CH_2$, =CH—$CH_3$, or =O.

In general, $R^3$ and $R^4$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, or $R^3$ and $R^4$ may be taken together to form a $C_1$-$C_5$ substituted or unsubstituted cycloalkyl, or $C_2$-$C_6$ substituted or unsubstituted aryl. In various embodiments, $R^3$ and $R^4$ are independently selected from a group consisting of hydrogen, deuterium, halogen, $C_1$-$C_4$ substituted or unsubstituted alkyl, $C_1$-$C_4$ substituted or unsubstituted alkoxy, or $R^3$ and $R^4$ may be taken together to form a or $C_1$-$C_5$ substituted or unsubstituted cycloalkyl, $C_2$-$C_6$ substituted or unsubstituted alkenyl, or $C_2$-$C_6$ substituted or unsubstituted aryl. In some embodiments, $R^3$ and $R^4$ are independently selected from a group comprising hydrogen, deuterium, methyl, ethyl, propyl, isopropyl, fluoromethyl, difluoromethyl, trifluoromethyl, fluoroethyl, difluoroethyl, trifluoroethyl, tetrafluoroethyl, pentafluoroethyl, bromine, chlorine, or fluorine, or $R^3$ and $R^4$ may be taken together to form a cyclopropyl, a cyclobutyl, a cyclohexyl, a cycloheptyl, or aryl. In specific embodiments, $R^3$ and $R^4$ are independently selected from a group comprising hydrogen, deuterium, methyl, trifluoromethyl, chlorine, fluorine, or $R^3$ and $R^4$ may be taken together to form an aryl.

Generally, $R^1$ and $R^3$ may be taken together to form a $C_1$-$C_6$ substituted or unsubstituted cycloalkyl, or $C_2$-$C_6$ substituted or unsubstituted cycloalkenyl, or $R^2$ and $R^3$ may be taken together to form a $C_1$-$C_6$ substituted or unsubstituted cycloalkyl, or $C_2$-$C_6$ substituted or unsubstituted cycloalkenyl. In various embodiments, $R^1$ and $R^3$ may be taken together to form a cyclopropyl, cyclobutyl, cyclopentyl, cyclohexyl, cycloheptyl, cyclopentenyl, or cyclohexenyl, or $R^2$ and $R^3$ may be taken together to form a cyclopropyl, cyclobutyl, cyclohexyl, cycloheptyl, cyclopentenyl, or cyclohexenyl. In some embodiments, $R^1$ and $R^3$ may be taken together to form a cyclopentyl or cyclohexyl, or $R^2$ and $R^3$ may be taken together to form cyclopentyl or cyclohexyl.

Generally, $R^5$, $R^6$, and $R^7$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, $C_1$-$C_6$ substituted or unsubstituted alkenyl. In various embodiments, $R^5$, $R^6$, and $R^7$ are independently selected from a group consisting of hydrogen, deuterium, halogen, $C_1$-$C_4$ substituted or unsubstituted alkyl, or $C_1$-$C_4$ substituted or unsubstituted alkoxy. In some embodiments, $R^5$, $R^6$, and $R^7$ are independently selected from a group consisting of hydrogen, deuterium, methyl, ethyl, chlorine, or fluorine. In specific embodiments, $R^5$, $R^6$, and $R^7$ are hydrogen or deuterium.

For example, the compounds comprising Formula (I) or a salt thereof may be selected from a group comprising:

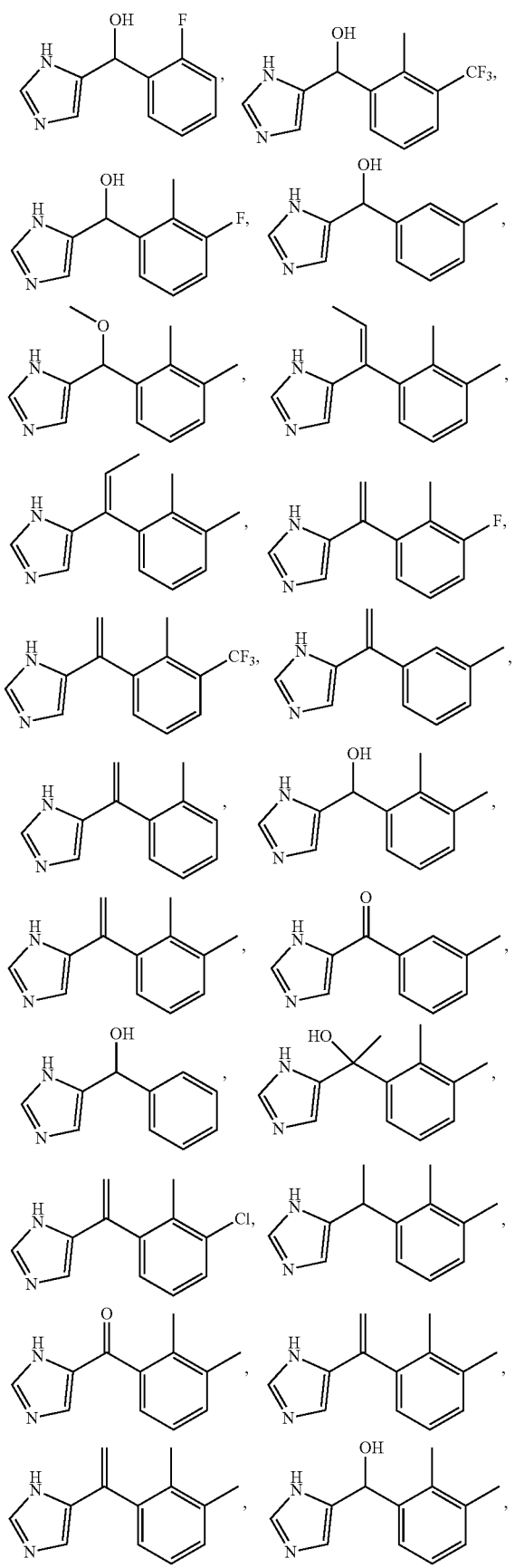
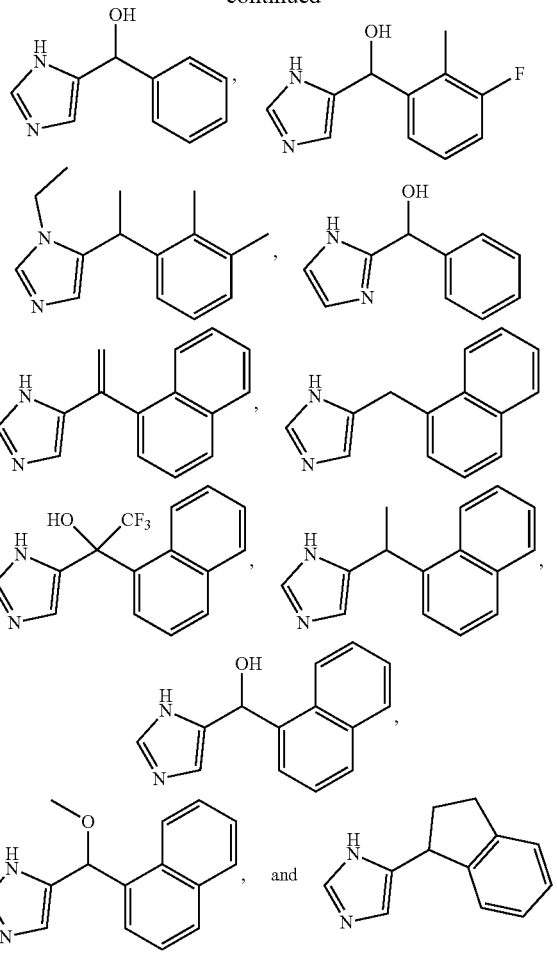

As appreciated by the skilled artisan, the compounds useful as an anthropod deterrent may have a low volatility. Low volatility of the compounds is necessary to ensure these compounds have a long residence time to effectively act as an arthropod deterrent without frequent reapplication. As appreciated by the skilled artisan, the volatility of the compound is directly related to the vapor pressure of the compound. At a given temperature, a compound having a higher vapor pressure vaporizes more readily than a compound having a lower vapor pressure. Thus, the higher volatility of a compound indicates a low boiling point of the compound. Conversely, a low volatility of a compound indicates a high boiling point of the compound. For a given compound, a predictive model may be used in calculating the boiling point. The predictive model method used in calculating the boiling point utilizes the computer program Estimation Program Interface Suite (EPI Suite™ Version 4.11, Stein, S. E. and Brown, R. L. 1994. *Estimation of normal boiling points from group contributions. J. Chem. Inf. Comput. Sci.* 34: 581-7.). Generally, to ensure low volatility according to EPI Suite™ Version 4.11, the calculated boiling point of compounds of Formula (I) or salts thereof may be at least 270° C. In various embodiments, the calculated boiling point of compounds of Formula (I) or salts thereof may be at least 270° C., at least 280° C., at least 290° C., or over 300° C.

In order for compounds of Formula (I) or salts thereof to be effective as an arthropod deterrent, these compounds must exhibit a high potency ($EC_{50}$ or $ED_{50}$) and high affinity ($K_i$ or $K_D$). Potency and affinity are measurements of the functional effect of the compound acting on the receptor. Affinity is the measurement of the strength of binding of the compound to the receptor. The potency and affinity refers to the concentration of the compound which induces a response halfway between the baseline and the maximum after a specified exposure time.

Generally, the compounds of Formula (I) or salt thereof may have potency ($EC_{50}$) of less than 1 µM. In various embodiments, the compounds of Formula (I) or salt thereof may have a potency of less than 1 µM, less than 100 nM, or less than 10 nM.

Selectivity is a comparative measure between affinities or potencies for a single drug or compound at two receptors. The larger the spread or separation between the curves at their half point the greater the fold change in the selectivity window between the wanted target receptor producing the desired effect and the unwanted off-target receptor producing undesired effects.

Generally, the compounds of Formula (I) or salts thereof exhibit a selectivity of at least 35 more selective for an arthropod octopamine receptor than for a vertebrate $\alpha_2$-Ar. In various embodiments, the compounds of Formula (I) or salts thereof exhibit a selectivity of at least 35 more selective, at least 100 times more selective, at least 500 times more selective, or at least 1000 times more selective for an arthropod octopamine receptor than for a vertebrate $\alpha_2$-Ar.

(II) Compositions Comprising Compounds of Formula (I) or salts thereof.

Another aspect of the present disclosure encompasses compositions comprising Formula (I) or salts thereof and at least one additional component wherein the additional components are selected from a group comprising fragrances, solvents, propellants, diluents, surfactants, thickeners, coatings, paints, or combinations thereof. Collectively, the additional components comprise the "carrier." Additionally, these compositions may further comprise at least one known arthropod deterrent providing an enhanced arthropod deterrent mixture. These compositions may be further formulated into a form which may be easily applied to an article or a subject.

(a) Compounds of Formula (I) or Salts Thereof.

The compounds of Formula (I) or salts thereof are described in Section I. In general, the composition comprising a compound of Formula (I) or a salt thereof contains the deterrent in an effective concentration.

The term "effective amount" describes an amount of deterrent present in a composition sufficient to produce a noticeable effect, such as a decreased frequency of mosquito bites. The effective amount can and will vary depending on many factors such as the arthropod or marine organism being deterred, severity of the infestation; individual subject parameters including age, physical condition, size and weight; concurrent treatments; area of treatments on the subject; the frequency of treatment; or the mode of administration. These factors are well known to those of ordinary skill in the art.

Generally, the concentration of the compound comprising Formula (I) or a salt thereof may range from about 0.0001% to 100% (w/w) of the total composition. In various embodiments, the concentration of the compound comprising Formula (I) or a salt thereof may range from about 0.0001% to 100%, from about 0.01% to about 75%, from about 0.1% to 50%, or from 1% to about 10% (w/w) of the total composition.

(b) Additional Components or "Carriers"

Depending on the final formulation used for the compositions comprising Formula (I) or a salt thereof, at least one additional component or carrier may be utilized in the composition.

(i) Fragrances

The composition may comprise a fragrance. Non-limiting examples of useful fragrances may be fruit fragrances such as strawberry, raspberry, peach, cherry, apple and pear; citrus fragrances such as orange, lemon, grapefruit, and lime; floral fragrances such as rose, hyacinth, lilac, lily-of-the-valley, calyx, osmanthus, orange blossom, apple blossom, rose, and freesia; woody fragrances such as cedarwood, sandalwood, oak, and pines; leather fragrances, oriental fragrances such as musk, vanillin, and laubdanum; and mint fragrances such as spearmint and peppermint.

Generally, amount of the fragrance may be about 0.25% and about 1% (w/w) of the total composition. In various embodiments, the amount of the fragrance may be about 0.25% to 1.0%, from about 0.4% to about 0.9%, or from 0.5% to about 0.7% (w/w) of the total composition.

(ii) Solvents

The composition may comprise a solvent. Non-limiting examples of suitable solvents are generally known within the art and may be lipophilic organic diluents, an alcohol, ethylene glycol, propylene glycol, dipropylene glycol, ether, oils including non-volatile and volatile liquids and oils, water, and combinations thereof. For example, the deterrent compound can be dissolved in a suitable alcohol and supplied in a liquid form such as a pump spray or for a plug-in diffuser. Non-limiting examples of suitable alcohols may be ethanol, propanol, isopropanol, butanol, isobutanol, pentanol, hexanol, heptanol, octanol, and phenyl ethyl alcohol. In one embodiment, the alcohols may comprise ethanol, isopropanol, butanol, and phenyl ethyl alcohol. In exemplary embodiments, the solvent comprises isopropanol.

In another embodiment, the alcohol solvent can be combined with water or a lipophilic organic diluent or carrier. Non-limiting examples of suitable alcohols which may be combined with water may be ethylene glycol, propylene glycol, dipropylene glycol, dipropylene glycol monoethyl ether, dipropylene glycol methyl ether, or Dow Corning® Q7-9180 silicone liquid. In an exemplary embodiment, the solvent may be a combination of water and an alcohol selected from ethanol or isopropanol.

Generally, the solvent present in the composition with the arthropod deterrent may range from about 0.5% to 99.99% (w/w) of the total composition. In various embodiments, the solvent present in the composition with the arthropod deterrent may range from about 0.5% and 99.99%, from about 1.0% to 90%, from about 5% to 80%, from about 10% to 70%, or from about 20% to 50% based on the total composition.

In general, the composition may also comprise water and may range from between about 70% to 99.99% (w/w) of the total composition. In various embodiments, the amount of water in the composition may range from about 70% to 99.99%, from about 75% to 99%, or from about 80% to 98.5% (w/w) of the total composition.

Generally, the alcohol present in the composition may range from about 1% and about 20% (w/w) of the total composition. In various embodiments, alcohol present in the composition may range from about 1% and about 20%, from about 1.25% to about 15%, or from about 1.5% and about 10% (w/w) of the total composition.

(iii) Propellants

The composition may comprise a propellant. Non-limiting examples of suitable propellants may be chlorofluorocarbons (CFC) such as trichloromonofluoromethane, dichlorodifluoromethane, and dichlorotetrafluoroethane; hydrochlorofluorocarbons (HCFC) or hydrofluorocarbons (HFC) such as chlorodifluoromethane, trifluoromonofluoroethane, chlorodifluoroethane, difluoroethane, and heptafluoropropane; hydrocarbons such as propane, butane, and isobutene; and other compressed gases such as nitrogen, carbon dioxide, and nitrous oxide, and combinations of the above-described propellants.

In one embodiment, the propellant may be propane. In another embodiment, the propellant may be 1,1-difluoroethane. The propellant may not comprise an inert gas of the tumorigenic compound class, which includes 1,1,1,2-tetrafluoroethane, chlorodifluoromethane, and dichlorodifluoromethane. The propellant may have a flashpoint of less than about −50° C.

Generally, when a propellant is included in the composition, the propellant may range from between about 75% to about 99.99% (w/w) of the total composition. In various embodiments, the propellant may range from about 75% to about 99.99%, from about 80% to 99%, from about 85% to 95%, or from about 90% to about 92% based on the total composition.

(iv) Surfactants

The composition may comprise a surfactant. Surfactants are generally used to produce compositions as emulsion. Either water-in-oil or oil-in-water emulsions may be formulated. In some embodiments, the surfactant may be an ionic surfactant, a nonionic surfactant, a cationic surfactant, an anionic surfactant, or a zwitterionic surfactant. Non-limiting examples of surfactants may be nonionic ethoxylated and nonethoxylated surfactants, abietic acid, almond oil PEG, beeswax, butylglucoside caprate, $C_{18}$-$C_{36}$ acid glycol ester, $C_9$-$C_{15}$ alkyl phosphate, caprylic/capric triglyceride PEG-4 esters, ceteareth-7, cetyl alcohol, cetyl phosphate, corn oil PEG esters, DEA-cetyl phosphate, dextrin laurate, dilaureth-7 citrate, dimyristyl phosphate, glycereth-17 cocoate, glyceryl erucate, glyceryl laurate, hydrogenated castor oil PEG esters, isosteareth-11 carboxylic acid, lecithin, lysolecithin, nonoxynol-9, octyldodeceth-20, palm glyceride, PEG diisostearate, PEG stearamine, poloxamines, polyglyceryls, potassium linoleate, PPG's, raffinose myristate, sodium caproyl lactylate, sodium caprylate, sodium cocoate, sodium isostearate, sodium tocopheryl phosphate, steareths, TEA-$C_{12}$-$C_{13}$ pareth-3 sulfate, tri-C12-C15 pareth-6 phosphate, trideceths, or combinations thereof.

(v) Thickeners

In certain applications, the composition may comprise a thickener or a viscosity modifier. Non-limiting examples of thickeners may be acrylamides copolymer, agarose, amylopectin, bentonite, calcium alginate, calcium carboxymethyl cellulose, carbomer, carboxymethyl chitin, cellulose gum, dextrin, gelatin, hydrogenated tallow, hydroxyethylcellulose, hydroxypropylcellulose, hydroxypropyl starch, isopropyl palm itate, magnesium alginate, methylcellulose, microcrystalline cellulose, pectin, various PEGs, polyacrylic acid, polymethacrylic acid, polyvinyl alcohol, various PPGs, sodium acrylates copolymer, sodium carrageenan, xanthan gum, yeast beta-glucan, or combinations thereof.

Generally, when present, the thickener may range from about 1% to about 30% (w/w) of the total composition. In various embodiments, the thickener may range from about for example between about 5% to about 20% (w/w) of the total composition, or from between about 10% to about 15% (w/w) of the total composition.

(vi) Paints or Coatings

In certain applications, the composition may comprise a paint, a coating, or combinations thereof. Non-limiting examples of paints and coatings may be a latex paint, an oil-based paint, a stain, a varnish, an epoxy resin coating, a primer coating, or combinations thereof.

Generally, when present, the paint or the coating may range from about 1% to about 99% (w/w) of the total composition. In various embodiments, the paint or the coating may range from about for example between about 1% to about 99% (w/w) of the total composition, or from between about 50% to about 95% (w/w) of the total composition.

(vii) Other Optional Components

In certain applications, other components may be added to the composition. Non-limiting examples of these optional components may be fillers, lubricants, colorants, pH modifiers, stabilizers, antioxidants, preservatives, nanoparticles of controlled release polymers, and other components known to the skilled artisan.

(c) Optional Known Deterrents

The composition, as described above, may further comprise an effective amount of an optional known deterrent. As discussed above, the "effective amount" of the optional known deterrent can and will vary as described previously. The skilled artisan would readily understand the amount of the optional commercial deterrent to be used in the composition. Non-limiting examples of optional known deterrents may be DEET, picaridin, PMD (active in Oil of Eucalytus), IR3535, SS-220 ((1S,2'S)methylpiperidinyl-3-cyclohexen-1-carboxamide), and similar compounds for terrestrial arthropods, and copper, zinc and other metals, Diuron™ (3-(3,4-dichlorophenyl)-I,I-dimethylurea), Irgarol 1051™ (2-methylthio-4-tert-butylamino-6-cyclopropylamino-s-triazine), zincpyrothione (Zinc, Ms(I-hydroxy-2(IH)-pyridinethionato-O,S)—, (T-4)-), copperpyrothione (Copper, Ms(I-hydroxy-2(IH)-pyridinethionato-O,S)—, (T-4)-), diclofluanide (N'-dimethyl-N-phenylsulphamide), zineb (zinc ethylene bisdithiocarbamate), Zinram™ (Zinc bis(dimethylthiocarbamates)) (3-5), quaternary ammonium compounds, SeaNine™ (4,5-dichloro-2-n-octyl-3(2H)-isothiazolone), EcoNea™ (2-(p-chlorophenyl)-3-cyano-4-bromo-5-trifluoromethyl), Selektop (medetomidine), or combinations thereof.

(d) Compositions for Administration

The compositions comprising compounds of Formula (I) or a salt thereof may be used in various forms for administration. In some embodiments, the composition may be used as a topical composition such as a spray, a foam, a shampoo, a dip, a diffuser, an aerosol, a gel, a cream, a lotion, or a spot-on composition.

In other embodiments, the deterrent compositions can be formulated with a paint or a coating. Non-limiting examples of suitable paints or coating may be latex paint, oil based paints, stains, primers, overcoats, epoxy resin based coatings, urethane based coatings, silicon based coatings, rosin based coatings, polymer coatings, various coatings for aquatic marine uses, and combinations thereof.

In an additional embodiment, the deterrent compositions may be incorporated into a solid carrier material to form a matrix composition containing the arthropod repellant, such as a fabric garment or a collar. The matrix containing the arthropod repellant may be formed into a collar as is well known and amply described in the art, for example in U.S. Pat. No. 3,852,416. Typically an admixture of an arthropod repellant and a carrier material providing the matrix is formed into strips through an extrusion process, and each strip is then formed a collar by including a fastening device such as a buckle, snap or hook. The solid carrier material forming the matrix into which the arthropod repellant is incorporated is for example a polymer or polymer mixture with suitable release characteristics so the deterrent is released from the collar. And the matrix containing the arthropod repellant may be formed into a fabric garment as described in the art, for example in U.S. Publication No. 2010/00319632.

Suitable polymers for forming a solid substrate for making a collar are well known and include, but are not limited to, polyethylene, polyvinyl acetate, ethylene acid copolymers, ethylene acrylates, polyurethanes, styrene-butadiene, polyvinyl butyral, polyvinyl chloride (PVC), polyolefin, polyacrylate, and polymethacrylate esters, and silicon polymer.

Plasticizers may be incorporated into the mixture to render the polymer resin more flexible. Suitable plasticizers include phosphoric acid esters (e.g. tricresyl phosphate) or phthalic acid esters (such as dioctyl phthalate or diisodecyl phthalate (DIDP)). The collar may also include other additives such as stabilizers, for example antioxidants to protect the collar material from degradation by UV light and other oxidizing factors.

(III) Method for Deterring Marine Biofouling Organisms using Compositions comprising the Compounds of Formula (I) or Salt Thereof Another aspect of the present disclosure encompasses methods for deterring marine organisms or preventing biofouling. The method comprises providing a deterrent composition comprising the compounds of Formula (I) or salt thereof, coating a surface of an article thus providing an effective concentration of the deterrent on the article, and curing the composition. The article, in broad terms, may be defined as a material to which the aquatic or marine organisms adhere.

In various embodiments, the marine organism, as defined herein, is an organism which causes biofouling. Non-limiting examples of such marine organisms may be barnacles, tubeworms, bivalves, marine maxillopoda, Polychaeta, bivalvia, or combinations thereof.

In various embodiments, the article may be an object which utilizes large amounts of fresh or saltwater, or has prolonged contact or permanent contact with fresh or saltwater in which the aquatic or marine organism lives and attaches. Non-limiting examples of these articles may be ship hulls, ship ballasts, heat exchangers, aquaculture ropes, fishing nets, cages, buoys, piers, underwater cables, underwater pipes, oil rig platforms, and water intake pipes for land based installations.

The deterrent composition comprising the compounds of Formula (I) or salt thereof may be applied to at least a portion of at least one surface of the article, on multiple surfaces of the article, or over every surface of the article. Generally, the deterrent composition comprising the compounds of Formula (I) or salt thereof may be applied and cured on one layer or multiple layers. In some embodiments, the composition comprising the compounds of Formula (I) or salt thereof may be applied and cured directly on the article.

The method further comprises applying the deterrent composition comprising the compounds of Formula (I) or salt thereof to a portion of at least one surface of an article. Suitable articles are detailed above. Application of the deterrent composition comprising the compounds of Formula (I) or salt thereof may be applied through various means. For example, the deterrent composition comprising the compounds of Formula (I) or salt thereof may be applied using a drawdown bar, a roller, a knife, a paint brush, a sprayer, by dipping, or other methods known to the skilled artisan. Also, more than one application of the deterrent composition comprising the compounds of Formula (I) or salt thereof may be applied. As detailed above, the deterrent composition comprising the compounds of Formula (I) or salt thereof may be applied to one or more surfaces of the article to be coated.

The method further comprises curing the deterrent composition comprising the compounds of Formula (I) or salt thereof to an article. In an embodiment, the deterrent composition comprising the compounds of Formula (I) or salt thereof of present invention can be cured to form a coating or layer on the article. For example, the deterrent composition comprising the compounds of Formula (I) or salt thereof of the present invention can be cured under conditions to form a film, a barrier, a coating, or a solid. Curing the deterrent composition comprising the compounds of Formula (I) or salt thereof may be carried out at conditions including a predetermined temperature and for a predetermined period of time sufficient to cure the composition. Generally, deterrent composition comprising the compounds of Formula (I) or salt thereof may be cured at a temperature from about room temperature (~23° C.) to about 100° C. to form the cured coating. In various embodiments, the deterrent composition comprising the compounds of Formula (I) or salt thereof may be cured at a temperature from about 23° C. to about 100° C., from about 30° C. to about 90° C., from about 40° C. to about 80° C., or from about 50° C. to about 70° C. Methods for curing the deterrent composition comprising the compounds of Formula (I) or salt thereof may be by a conventional manner or by a method known by one skilled in the art. Generally, the duration of heating steps, if needed, may be from 5 minute to 12 hours. In various embodiments, the duration of heating step may be from about 5 minutes to 12 hours, from about 30 minutes to 5 hours, or from about 1 hour to 2 hour.

After the deterrent composition comprising the compounds of Formula (I) or salt thereof is cured, the resulting article may exhibit improved biofouling capabilities.

(IV) Method for Deterring Terrestrial Arthropods using Compositions comprising the Compounds of Formula (I) or Salt Thereof Another aspect of the present disclosure encompasses methods of deterring terrestrial arthropods. The method comprises providing a composition comprising the compounds of Formula (I) or salt thereof and applying to a surface of a subject thus providing an effective concentration of the arthropod deterrent on the subject.

In various embodiments, the terrestrial arthropod, as defined herein, is an arthropod which causes stinging or biting. Non-limiting examples of such terrestrial arthropods may be mosquito, a tick, a fly, a cockroach, an arachnid, or an insect.

Suitable subjects, as defined herein, includes a human, a livestock animal, a companion animal, a lab animal, or a zoological animal. In one embodiment, the subject may be a rodent. Non-limiting examples of rodents may be a mouse, a rat, or a guinea pig. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, bears, elephants, hippopotamuses, rhinoceros, deer, gazelle, giraffes, ostrich, emus, snakes, alligators, crocodiles, mammals, marsupials, amphibians, reptiles, and birds. In an embodiment, the animal is a laboratory animal. Non-limiting examples of a laboratory animal may include rodents, canines, felines, and non-human primates. In preferred embodiments, the subject is a human.

The deterrent composition comprising the compounds of Formula (I) or salt thereof may be applied to at least a portion of the subject being affected by the terrestrial arthropod. Non-limiting methods of applying the composition comprising the compounds of Formula (I) or salt thereof may be spraying the deterrent composition on the subject (as with an aerosol, spray, diffuser), applying the deterrent composition topically as a foam, a gel, a cream, a lotion, utilizing the composition as a dip or shampoo, or using the composition as a spot-on deterrent composition.

(V) Process for Preparing Compounds of Formula (I) or Salt Thereof

In another aspect of the present disclosure encompasses processes for preparing compounds of Formula (Ia) or a salt thereof. The process comprises contacting a compound of Formula (III) with a compound of Formula (IV) to form a compound of Formula (V). The process further comprises contacting a compound of Formula (V) with a compound of Formula (VI) to form a compound of Formula (Ia). The process for preparing the compound of Formula (Ia) is illustrated as follows:

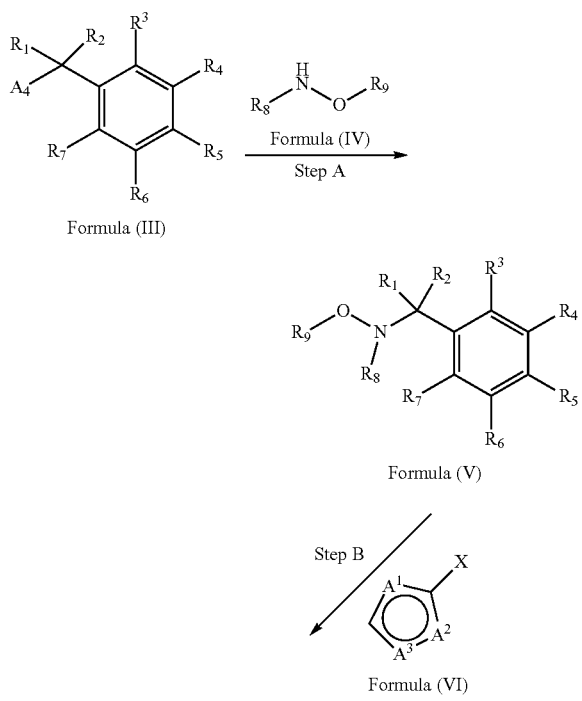

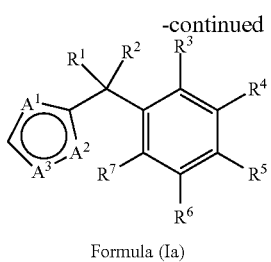

Formula (Ia)

wherein:
$A^1$, $A^2$, $A^3$, and $A^4$ are independently selected from a group consisting of C, N, O, and S;
$R^1$ and $R^2$ are taken together as $=O$;
$R^3$, $R^4$, $R^5$, $R^6$, and $R^7$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, or $R^3$ and $R^4$ may be taken together to form a $C_1$-$C_5$ substituted or unsubstituted cycloalkyl, or $C_2$-$C_6$ substituted or unsubstituted cycloalkenyl; and $R^8$ and $R^9$ are independently selected from a group consisting of hydrogen, or $C_1$-$C_6$ substituted or unsubstituted alkyl; and X is a halogen.

In further embodiments, $A^1$ and $A^2$ are N, $A^3$ is C, and $A^4$ is hydroxyl; $A^1$ and $A^3$ are N, $A^2$ is C, and $A^4$ is hydroxyl; or $A^1$, $A^2$, and $A^3$ are N, and $A^4$ is hydroxyl. In preferred embodiments, $A^1$ and $A^2$ are N, $A^3$ is C, and $A^4$ is hydroxyl; $A^1$ and $A^3$ are N, $A^2$ is C, and $A^4$ is hydroxyl.

In various embodiments, $R^1$ and $R^2$ may be taken together as $=O$.

In some embodiments, $R^3$ and $R^4$ are independently selected from a group consisting of hydrogen, deuterium, halogen, $C_1$-$C_4$ substituted or unsubstituted alkyl, $C_1$-$C_4$ substituted or unsubstituted alkoxy, or $R^3$ and $R^4$ may be taken together to form a $C_1$-$C_5$ substituted or unsubstituted cycloalkyl or $C_3$-$C_5$ substituted or unsubstituted cycloalkenyl. In specific embodiments, $R^3$ and $R^4$ are independently selected from a group consisting of hydrogen, deuterium, methyl, trifluoromethyl, chlorine, or fluorine.

In various embodiments, $R^5$, $R^6$, and $R^7$ are independently selected from a group consisting of hydrogen, deuterium, halogen, $C_1$-$C_4$ substituted or unsubstituted alkyl, or $C_1$-$C_4$ substituted or unsubstituted alkoxy. In specific embodiments, $R^5$, $R^6$, and $R^7$ are independently selected from a group consisting of hydrogen, deuterium, methyl, ethyl, chlorine, or fluorine.

In other embodiments, $R^8$ and $R^9$ are independently selected from a group consisting of $C_1$-$C_4$ substituted or unsubstituted alkyl; and X is chlorine, bromine, or iodine. In specific embodiments, $R^8$ and $R^9$ are methyl, and X is iodine.

(a) Step A of the Process.

Step A of the process involves contacting a substituted benzoic acid of Formula (III) with the substituted hydroxyl amine or salt thereof of Formula (IV) in the presence of an acyl coupling reagent or an acyl activation reagent.

(i) Substituted Benzoic Acid.

The substituted benzoic acid of Formula (III) is detailed above. In some embodiments, $R^3$, $R^4$, $R^5$, $R^6$, and $R^7$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, or $R^3$ and $R^4$ may be taken together to form a $C_1$-$C_5$ substituted or unsubstituted cycloalkyl, or $C_2$-$C_6$ substituted or unsubstituted cycloalkenyl. In certain embodiments, $R^3$, $R^4$, $R^5$, $R^6$, and $R^7$ are independently selected from a group consisting of hydrogen, deuterium, halogen, $C_1$-$C_4$ substituted or unsubstituted alkyl, $C_1$-$C_4$ substituted or unsubstituted alkoxy, or $R^3$ and $R^4$ may be taken together to form a $C_1$-$C_5$ substituted or unsubstituted cycloalkyl or a substituted or unsubstituted aryl. In preferred embodiments, $R^3$ and $R^4$ are independently selected from a group consisting of hydrogen, deuterium, methyl, trifluoromethyl, chlorine, fluorine; and $R^5$, $R^6$, and $R^7$ are independently selected from a group consisting of hydrogen, deuterium, methyl, ethyl, chlorine, or fluorine. Non-limiting examples of substituted benzoic acids may be 2-fluorobenzoic acid, 3-chloro-2-methylbenzoic acid, 3-fluoro-2-methylbenzoic acid, 3-methylbenzoic acid, 3-trifluoromethyl-2-methylbenzoic acid, or benzoic acid.

(ii) Substituted Hydroxylamine Compound

The substituted hydroxyl amine compound is detailed above. In some embodiments, $R^8$ and $R^9$ are independently selected from a group consisting of $C_1$-$C_4$ substituted or unsubstituted alkyl. In other embodiments, $R^8$ and $R^9$ are independently selected from a group consisting of methyl, ethyl, or propyl. In specific embodiments, $R^8$ and $R^9$ are methyl.

Generally, the molar ratio of the substituted benzoic acid to the substituted hydroxyl amine may range from 1.0:0.5 to about 1.0:2.0. In various embodiments, molar ratio of the substituted benzoic acid to the substituted hydroxyl amine may range from 1.0:0.5 to about 1.0:2.0, from about 1.0:0.75 to about 1.0:1.5, or from about 1.0:0.9 to about 1.0:1.1.

(iii) Acyl Coupling or Activation Reagent

A wide variety of acyl coupling reagents or acyl activation reagents may be used in the process. As appreciated by the skilled artisan, the acyl coupling reagent or activation reagent converts the hydroxyl group of the substituted benzoic acid into a highly active leaving group which will react more readily with the substituted hydroxylamine compound. Non-limiting acyl coupling reagents or activation reagents may be thionyl chloride, oxalyl chloride, phosphorus pentachloride, phosphorus oxychloride, phosphorus trichloride, cyanuric chloride, diphenylphosphonic azide, carbonyl diimidazole, carbonyl ditriazole, a carbodiimide, an anhydride, a chloroformate, a boron reagent, phosphonium salts, or combinations thereof. In a preferred embodiment, the acyl coupling reagent or acyl activation reagent may be a carbodiimide, namely N-(3-dimethylaminopropyl)-N'-ethylcarbodiimide or a salt thereof.

Generally, the molar ratio of the substituted benzoic acid to the acyl coupling reagent may range from 1.0:0.5 to about 1.0:2.0. In various embodiments, molar ratio of the substituted benzoic acid to the acyl coupling reagent or activation reagent may range from 1.0:0.5 to about 1.0:2.0, from about 1.0:0.75 to about 1.0:1.5, or from about 1.0:0.9 to about 1.0:1.1.

(iv) Optional Amine

In some embodiments, the process may further comprise an amine. Depending on the starting substrates, the amine may be a secondary amine, a tertiary amine, or combinations thereof. Non-limiting examples of suitable secondary amines include ethyl methyl amine, dimethyl amine, diethyl amine, dicyclohexyl amine, methyl cyclohexyl amine, phenyl ethyl amine, dibenzyl amine, methyl benzyl amine, ethyl benzyl amine, cyclohexyl phenyl amine, dibutyl amine, ditertiarybutyl amine, dipropyl amine, dipentylamine, dicyclohexyl amine, piperidine, 2-methylpiperidine, 2,5-dimethylpiperidine, 2,6-dimethylpiperidine, piperazine, 2-methylpiperazine, 2,6-dimethylpiperazine, and morpholine. Non-limiting examples of suitable tertiary amines include trimethylamine, triethylamine, diisopropylethylamine, tripropylamine, tributylamine, 4-methylmorpholine, 4-ethylmorpholine, N-methylpyrrolidine, N-methylpiperidine, pyrazine, 4-dimethylaminopyridine, pyridine, and 2,6-lutidine.

The molar ratio of the acyl coupling or activation reagent to the amine may vary depending on acyl coupling or activation reagent of the process. In general, the molar ratio of the acyl coupling or activation reagent to the amine will range from about 1.0:0.9 to about 1.0:1.1. In certain embodiments, the molar ratio of the acyl coupling or activation reagent to the amine may range from about 1.0:0.9 to about 1.0:1.1, from about 1.0:0.95 to about 1.0:1.05, or from about 1.0:0.98 to about 1.0:1.02.

(v) Solvent

The process, as detailed herein, may also comprise a solvent. The solvent can and will vary depending on the starting substrates used in the process. The solvent may be a polar protic solvent, a polar aprotic solvent, a non-polar solvent, or combinations thereof. Suitable examples of polar protic solvents include, but are not limited to, water; alcohols such as methanol, ethanol, isopropanol, n-propanol, isobutanol, n-butanol, s-butanol, t-butanol, and the like; diols such as ethylene glycol, propylene glycol; polyols such as glycerol, mannitol, sorbitol; organic acids such as formic acid, acetic acid, and so forth; amines such as trimethylamine, or triethylamine, and the like; amides such as formamide, acetamide, and so forth; and combinations of any of the above. Non-limiting examples of suitable polar aprotic solvents include acetonitrile, dichloromethane (DCM), diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (THF), 2-methyltetrahydrofuran, trichloromethane, and combinations thereof. Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof.

In general, the volume to weight ratio of the solvent to the compound of Formula (III) will range from about 1.0:1 to about 50:1. In various embodiments, the volume to weight ratio of the solvent to the compound of Formula (III) may range from about 1.0:1 to about 2:1, from about 2:1 to about 5:1, from about 5:1 to about 25:1, or from about 25:1 to about 50:1. In a preferred embodiment, the volume to weight ratio of the solvent to the compound of Formula (III) may range from about 2:1 to about 10:1.

(vi) Reaction Conditions

In general, the reaction of step A will be conducted at a temperature that ranges from about 0° C. to about 1500° C. In various embodiments, the temperature of the reaction may range from about 0° C. to about 150° C., from about 20° C. to about 120° C., from about 40° C. to about 100° C., or from about 50° C. to about 75° C. In one embodiment, the reaction may be conducted at temperature that ranges from about 20° C. to about 50° C. or from about 35° C. to about 45° C. In another embodiment, the temperature of the reaction may be about room temperature (~23° C.). The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as chromatography (e.g., HPLC or TLC). The duration of the reaction can and will vary depending many factors, such as the starting substrates, the solvent of the reaction, and the temperature used in the process. The duration of the reaction may range from about 5 minutes to about 48 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours, from about 24 hours to about 36 hours, or from about 36 hours to about 48 hours. In this context, a "completed reaction" generally means that the reaction mixture contains a significantly diminished amount of the compound of Formula (III). Typically, the amount of the compound of Formula (III) remaining in the reaction mixture at the end of the reaction may be less than about 10%, less than about 5%, or less than about 2%.

The compound of Formula (V) may have a yield of at least about 25%. In various embodiments, the compound of Formula (V) may have a yield of at least about 25%, a yield of at least about 30%, a yield of at least about 40%, a yield of at least about 50%, at least about 60%, at least about 65%, at least about 70%, at least about 75%, at least about 80%, at least about 85%, at least about 90%, at least about 95%, or at least about 99%.

(b) Step B in the Process

Step B in the process involves contacting the benzamide of Formula (V) with a heterocyclic compound of Formula (VI) in the presence of a Grignard reagent.

(i) Heterocyclic Compound

The heterocyclic compound of Formula (VI) is detailed above. In some embodiments, $A^1$ and $A^2$ are N and $A^3$ is C, $A^1$ and $A^3$ are N and $A^2$ is C, or $A^1$, $A^2$, and $A^3$ are N; and X is chlorine, bromine, or iodine. In certain embodiments, $A^1$ and $A^2$ are N and $A^3$ is C, $A^1$ and $A^3$ are N and $A^2$ is C; and X is iodine. As appreciated by the skilled artisan, the heterocyclic compound of Formula (VI) may further comprise a nitrogen protecting group. Non-limiting examples of nitrogen protecting groups may be a t-butoxycarbonyl (BOC), benzyloxycarbonyl (CBZ), or triphenylmethyl (trityl). A variety of nitrogen protecting groups and the synthesis thereof may be found in "Greene's Protective Groups in Organic Synthesis," 4$^{th}$ Ed. by P.G.M. Wuts and T.W. Greene, John Wiley & Sons, Inc., 2007. In an embodiment, the heterocyclic compound of Formula (VI) is 4-iodo-1-tritylimidazole Generally, the molar ratio of the substituted benzamide to the heterocyclic compound may range from 1.0:0.5 to about 1.0:2.0. In various embodiments, molar ratio of the benzamide to the heterocyclic compound may range from 1.0:0.5 to about 1.0:2.0, from about 1.0:0.75 to about 1.0:1.5, or from about 1.0:0.9 to about 1.0:1.1.

(ii) Grignard Reagent

A wide variety of Grignard reagents may be used in the process. Non-limiting examples of Grignard reagents may be methylmagnesium chloride, methylmagnesium bromide, methylmagnesium iodide, ethylmagnesium chloride, ethylmagnesium bromide, ethylmagnesium iodide, butylmagnesium chloride, butylmagnesium bromide, butylmagnesium iodide, phenylmagnesium chloride, phenylmagnesium bromide, phenylmagnesium iodide, allylmagnesium chloride, allylmagnesium bromide, or allylmagesium iodide.

Generally, the molar ratio of the heterocyclic compound to the Grignard reagent may range from 1.0:0.5 to about 1.0:2.0. In various embodiments, molar ratio of the heterocyclic compound to the Grignard reagent may range from 1.0:0.5 to about 1.0:2.0, from about 1.0:0.75 to about 1.0:1.5, or from about 1.0:0.9 to about 1.0:1.1.

(iii) Solvent

The process, as detailed herein, may also comprise a solvent. The solvent can and will vary depending on the starting substrates used in the process. The solvent may be a polar aprotic solvent, a non-polar solvent, or combinations thereof. Non-limiting examples of suitable polar aprotic solvents include acetonitrile, diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, nitrobenzene, nitromethane, propionitrile, sulfolane, tetramethylurea, tetrahydrofuran (THF), 2-methyltetrahydrofuran, and combinations thereof. Suitable examples of non-polar solvents include, but are not limited to, alkane and substituted alkane solvents (including cycloalkanes), aromatic hydrocarbons, ethers, corn binations thereof, and the like. Specific non-polar solvents that may be employed include, for example, benzene, t-butyl methylether, cyclohexane, diethyl ether, diethylene glycol, fluorobenzene, heptane, hexane, methyltetrahydrofuran, pentyl acetate, tetrahydrofuran, toluene, and combinations thereof.

In general, the volume to weight ratio of the solvent to the compound of Formula (VI) will range from about 1.0:1 to about 50:1. In various embodiments, the volume to weight ratio of the solvent to the compound of Formula (VI) may range from about 1.0:1 to about 2:1, from about 2:1 to about 5:1, from about 5:1 to about 25:1, or from about 25:1 to about 50:1. In a preferred embodiment, the volume to weight ratio of the solvent to the compound of Formula (VI) may range from about 2:1 to about 10:1.

(vi) Reaction Conditions

In general, the reaction of step B will be conducted at a temperature that ranges from about 0° C. to about 150° C. In various embodiments, the temperature of the reaction may range from about 0° C. to about 150° C., from about 20° C. to about 120° C., from about 40° C. to about 100° C., or from about 50° C. to about 75° C. In one embodiment, the reaction may be conducted at temperature that ranges from about 20° C. to about 50° C. or from about 35° C. to about 45° C. In another embodiment, the temperature of the reaction may be about room temperature (~23° C.). The reaction typically is performed under ambient pressure. The reaction may also be conducted under an inert atmosphere, for example under nitrogen, argon or helium.

Generally, the reaction is allowed to proceed for a sufficient period of time until the reaction is complete, as determined by any method known to one skilled in the art, such as chromatography (e.g., HPLC or TLC). The duration of the reaction can and will vary depending many factors, such as the starting substrates, the solvent of the reaction, and the temperature used in the process. The duration of the reaction may range from about 5 minutes to about 48 hours. In some embodiments, the duration of the reaction may range from about 5 minutes to about 30 minutes, from about 30 minutes to about 2 hours, from about 2 hours to about 4 hours, from about 4 hours to about 10 hours, from about 10 hours to about 15 hours, or from about 15 hours to about 24 hours, from about 24 hours to about 36 hours, or from about 36 hours to about 48 hours. In this context, a "completed reaction" generally means that the reaction mixture contains a significantly diminished amount of the compound of Formula (III). Typically, the amount of the compound of Formula (III) remaining in the reaction mixture at the end of the reaction may be less than about 10%, less than about 5%, or less than about 2%.

The compound of Formula (V) may have a yield of at least about 25%. In various embodiments, the compound of Formula (V) may have a yield of at least about 25%, a yield of at least about 30%, a yield of at least about 40%, a yield of at least about 50%, at least about 60%, at least about 65%, at least about 70%, at least about 75%, at least about 80%, at least about 85%, at least about 90%, at least about 95%, or at least about 99%.

(c) Compound of Formula (Ib)

The process further comprises step C, conversion of the compound of Formula (Ia) into the compound of Formula (Ib). The process for preparing compound of Formula (Ib) is illustrated as follows:

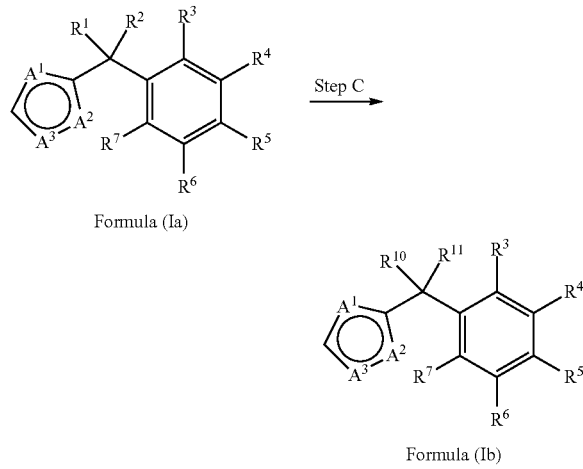

Formula (Ia)

Formula (Ib)

wherein $A^1$, $A^2$, $A^3$, $R^3$, $R^4$, $R^5$, $R^6$, and $R^7$ are defined above; and wherein $R^{10}$ and $R^{11}$ of Formula (Ib) are independently selected from a group consisting of hydrogen, deuterium, hydroxyl, $C_1$-$C_6$ substituted or unsubstituted alkyl, $C_2$-$C_6$ substituted or unsubstituted alkenyl, $C_1$-$C_6$ substituted or unsubstituted alkoxy; or $R^{10}$ and $R^{11}$ may be taken together to form a $C_1$-$C_6$ substituted or unsubstituted alkenyl, $R^3$ and $R^{10}$ may be taken together to form a $C_1$-$C_6$ substituted or unsubstituted cycloalkyl, or $C_2$-$C_6$ substituted or unsubstituted cycloalkenyl, $R^3$ and $R^{11}$ may be taken together to form a $C_1$-$C_6$ substituted or unsubstituted cycloalkyl, or $C_2$-$C_6$ substituted or unsubstituted cycloalkenyl.

In some embodiments, $R^{10}$ and $R^{11}$ are independently selected from a group consisting of hydrogen, deuterium, hydroxyl, $C_1$-$C_3$ substituted or unsubstituted alkyl, $C_2$-$C_4$ substituted or unsubstituted alkenyl, $C_1$-$C_4$ substituted or unsubstituted alkoxy; $R^{10}$ and $R^{11}$ may be taken together to form a $C_2$-$C_4$ substituted or unsubstituted alkenyl; $R^3$ and $R^{10}$ may be taken together to form a cyclopropyl, cyclobutyl, cyclopentyl, cyclohexyl, cycloheptyl, cyclopentenyl, or cyclohexenyl; or $R^3$ and $R^{11}$ may be taken together to form a cyclopropyl, cyclobutyl, cyclopentyl, cyclohexyl, cycloheptyl, cyclopentenyl, or cyclohexenyl. In specific embodiments, $R^{10}$ and $R^{11}$ are independently selected from a group consisting of hydrogen, methyl, ethyl, propyl, isopropyl, methoxy, ethoxy, propoxy, isopropoxy, hydroxyl, —$CH_2CH$=$CH_2$, —$CH_2C(CH_3)$=$CH_2$, —$CH$=$C(CH_3)_2$, —$CH$=$CHCH_3$; $R^{10}$ and $R^{11}$ may be taken together to form =$CH_2$, =$CHCH_3$, or =$C(CH_3)_2$; $R^3$ and $R^{10}$ may be taken together to form a cyclopentyl or cyclohexyl, or $R^3$ and $R^{11}$ may be taken together to form a cyclopentyl or cyclohexyl.

Generally, the process for converting the compound of Formula (Ia) into Formula (Ib) comprises contacting the compound of Formula (Ia) with a reagent which converts the ketone functionality into a the compound of Formula (Ib). The skilled artisan readily knows many methods for converting the ketone functionality into various analogs and conditions useful to make these analogs. Generally, these methods comprise at least one synthetic step. Some non-limiting examples are shown below.

(i) Secondary Alcohol Formation by Ketone Reduction

The ketone functionality in Formula (Ia) ($R^1$ and $R^2$ are taken together as =O) may be converted into an alcohol in Formula (Ib) ($R^{10}$ and $R^{11}$ are independently selected from a group consisting of hydrogen and hydroxyl). Non-limiting examples of suitable reducing agents may be lithium aluminum hydride, sodium borohydride, sodium cyanoborohydride, and catalytic reduction using a transition metal catalyst and hydrogen source. Suitable solvents and reaction conditions are described above in Section (V)(a)(v) and (V)(a)(vi).

(ii) Alkene Formation using a Wittig Reagent

The ketone functionality in Formula (Ia) ($R^1$ and $R^2$ are taken together as =O) may be converted into an alkene in Formula (Ib) ($R^{10}$ and $R^{11}$ are taken together to form a $C_1$-$C_6$ substituted or unsubstituted alkenyl). The process involves contacting the ketone with a Wittig reagent or a Horner-Wadsworth-Emmons reagent. Non-limiting examples of Wittig reagents or Horner-Wadsworth-Emmons reagent may be methyltriphenylphosphonium chloride, methyltriphenylphosphonium bromide, ethyltriphenylphosphonium chloride, ethyltriphenylphosphonium bromide, propyltriphenylphosphonium chloride, propyltriphenylphosphonium bromide, isopropyltriphenylphosphonium chloride, isopropyltriphenylphosphonium bromide, butyltriphenylphosphonium chloride, butyltriphenylphosphonium bromide, diethoxyphosphinyl)acetic acid ethyl ester, and ethoxycarbonylmethylphosphonic acid dimethylester. Suitable solvents and reaction conditions are described above in Section (V)(a)(v) and (V)(a)(vi).

(iii) Grignard Reaction with Ketone forming a Tertiary Alcohol

The ketone functionality in Formula (Ia) ($R^1$ and $R^2$ are taken together as =O) may be converted into an alcohol in Formula (Ib) ($R^{10}$ and $R^{11}$ are independently selected from a group consisting of $C_1$-$C_6$ substituted or unsubstituted alkyl and hydroxyl). This process involves contacting the ketone with a Grignard reagent. Non-limiting examples of Grignard reagents may be methylmagenesium chloride, methyl magnesium bromide, ethyl magnesium bromide, butyl magnesium iodide, hexyl magnesium iodide. Suitable solvents and reaction conditions are described above in Section (V)(a)(v) and (V)(a)(vi).

(iv) Ether Formation from the Secondary Alcohol or Tertiary Alcohol.

The secondary alcohol defined above in Section (V)(c)(i) ($R^{10}$ and $R^{11}$ are independently selected from a group consisting of hydrogen and hydroxyl) may be converted into an ether ($R^{10}$ and $R^{11}$ are independently selected from a group consisting of hydrogen and $C_1$-$C_6$ substituted or unsubstituted alkoxy). The process involves contacting the secondary alcohol with a reagent in the presence of a base to form an ether. Non-limiting examples of these reagents may be methyl chloride, methyl bromide, methyl iodide, dimethylsulfate, propyl iodide, methoxy methyl chloride, and methyl triflate. Suitable solvents and reaction conditions are described above in Section (V)(a)(v) and (V)(a)(vi).

(v) Alkane Formation from the Alkene

The alkene of Formula (Ib) ($R^{10}$ and $R^{11}$ are taken together to form a $C_2$-$C_6$ substituted or unsubstituted alkenyl) may be converted into the alkane ($R^{10}$ and $R^{11}$ are independently selected from a group consisting of hydrogen and $C_1$-$C_6$ substituted or unsubstituted alkane. The process involves contacting the alkene with a transition metal catalyst in the presence of a hydrogen source. Non-limiting examples of suitable catalysts may be palladium on carbon, palladium on barium sulfate, palladium acetate, and platinum on carbon. Non-limiting examples of hydrogen sources may be hydrogen gas, ammonium formate, and sodium formate. Suitable solvents and reaction conditions are described above in Section (V)(a)(v) and (V)(a)(vi).

(d) Salts of Formula (Ia) and Formula (Ib)

The compounds of Formula (Ia) and Formula (Ib) may be converted onto a variety of salts. Methods to prepare salts are known in the arts. Non-limiting examples of these salts may be acetate, aspartate, benzoate, bitartrate, citrate, formate, gluconate, glucuronate, glutamate, fumarate, hydrochloride, hydrobromide, hydroiodide, hypophosphite, hydrosulfate, isobutyrate, isocitrate, lactate, malate, maleate, meconate, methylbromide, methanesulfonate, monohydrate, mucate, nitrate, oxalate, phenylpropionate, phosphate, phthalate, propionate, pyruvate, salicylate, stearate, succinate, sulfate, tannate, tartrate, terephthalate, valerate, and the like.

(VI) Compounds Comprising Formula (II)

Another aspect of the disclosure encompasses compounds of Formula (II) or a salts thereof which may be useful as arthropod deterrents:

$R^7$, and $R^8$ each independently selected from a group comprising of hydrogen, halogen, or $C_1$-$C_6$ substituted or unsubstituted alkyl.

Generally, $R^1$, $R^2$, and $R^3$ are independently selected from a group is selected from a group consisting of hydrogen, hydroxyl, $C_1$-$C_6$ substituted or unsubstituted alkyl; $C_1$-$C_6$ substituted or unsubstituted alkenyl, $C_1$-$C_6$ substituted or unsubstituted alkoxy, and $R^1$ and $R^2$ may be taken together to form a $C_2$-$C_4$ substituted or unsubstituted alkenyl, or =O. In various embodiments, wherein $R^1$, $R^2$, and $R^3$ are independently selected from a group is selected from a group consisting of hydrogen, hydroxyl, $C_1$-$C_4$ substituted or unsubstituted alkyl, $C_1$-$C_4$ substituted or unsubstituted alkenyl, $C_1$-$C_4$ substituted or unsubstituted alkoxy, or $R^1$ and $R^2$ may be taken together to form a $C_2$-$C_4$ substituted or unsubstituted alkenyl, or =O. In some embodiments, $R^1$, $R^2$, and $R^3$ are independently selected from a group is selected from a group consisting of —H, —$CH_3$, —OH, —$CH_2NH_2$, —$CHCH_3NH_2$, —$C(CH_3)_2NH_2$, —$CH_2NHCH_3$, —$CH_2N(CH_3)_2$, —$CH_2OH$, —$CHCH_3OH$, $C(CH_3)_2OH$, —$CH_2OCH_3$, —$CH_2OCH_2CH_3$, —$CH_2CN$, —$CH(CN)_2$, —$CH_2CH_2F$, —$CH_2CHF_2$, —$CH_2CF_3$, —$CH_2CH_2Cl$, —$CH_2CHCl_2$, —$CH_2CCl_3$, —$CH_2SOCH_3$, —$CH_2SO_2CH_3$, —$CH(OH)CH_2NH_2$, —$CCH_3OHCH_2NH_2$, —$CH(OH)CH_2N(CH_3)_2$, —$CH(OH)CH_2NHCH_3$, —$CH(OH)CH_2NHCH(CH_3)_2$, —$CH(OH)CH_2NHCH_2CH_3$, —$CH(OH)CH_2NHCH(CH_3)CH_2CH_3$, —$CH(OH)CH_2NHCH(CH_3)CH_2CH_2C_6H_5$, —$CH(OH)CH_2NHCH(CH_3)CH_2CH_2C_6H_4OH$.

In general, $R^4$ is selected from a group comprising of hydrogen, halogen, $C_1$-$C_6$ alkyl, $C_1$-$C_6$ halogenated alkyl. In various embodiments, $R^4$ is selected from a group consisting hydrogen or $C_1$-$C_4$ substituted or unsubstituted alkyl. In some embodiments, $R^4$ is selected from a group consisting of hydrogen, methyl, ethyl, propyl, or isopropyl. In specific embodiments, $R^4$ is hydrogen.

Generally, $R^5$, $R^6$, $R^7$, and $R^8$ are independently selected from a group comprising of hydrogen, halogen, $C_1$-$C_6$ alkyl, $C_1$-$C_6$ halogenated alkyl. In various embodiments, $R^5$, $R^6$, $R^7$, and $R^8$ are independently selected from a group consisting of hydrogen, halogen, $C_1$-$C_4$ substituted or unsubstituted alkyl, or $C_1$-$C_4$ halogenated alkyl. In specific embodiments, $R^5$, $R^6$, $R^7$, and $R^8$ each independently selected from a group consisting of hydrogen, iodine, bromine, chlorine, fluorine, methyl, fluoromethyl, difluoromethyl, or trifluoromethyl.

For example, the compounds comprising Formula (II) or a salt thereof may be selected from a group comprising:

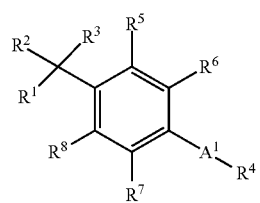

Formula (II)

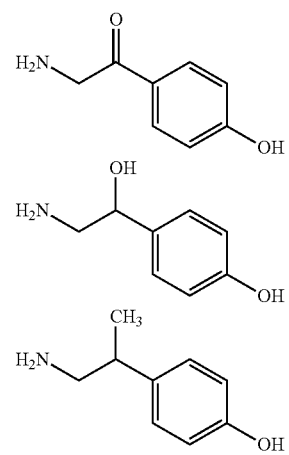

wherein $A^1$ is selected from a group consisting of nitrogen, oxygen, and sulfur;

$R^1$, $R^2$, and $R^3$ are independently selected from a group is selected from a group consisting of hydrogen, hydroxyl, $C_1$-$C_6$ substituted or unsubstituted alkyl; $C_1$-$C_6$ substituted or unsubstituted alkenyl, $C_1$-$C_6$ substituted or unsubstituted alkoxy, or $R^1$ and $R^2$ may be taken together to form a $C_2$-$C_4$ substituted or unsubstituted alkenyl, or =O, and $R^4$, $R^5$, $R^6$, -continued

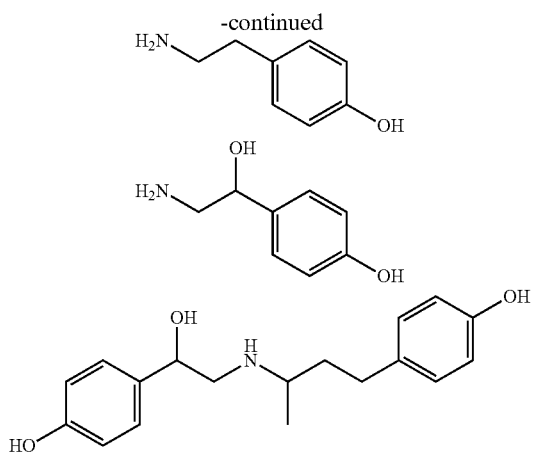

As appreciated by the skilled artisan, the compounds useful as an anthropod deterrent may have a low volatility. Low volatility of the compounds is necessary to ensure these compounds have a long residence time to effectively act as an arthropod deterrent without frequent reapplication. As appreciated by the skilled artisan, the volatility of the compound is directly related to the vapor pressure of the compound. At a given temperature, a compound having a higher vapor pressure vaporizes more readily than a compound having a lower vapor pressure. Thus, the higher volatility of a compound indicates a low boiling point of the compound. Conversely, a low volatility of a compound indicates a high boiling point of the compound. For a given compound, a predictive model may be used in calculating the boiling point. The predictive model method used in calculating the boiling point utilizes the computer program Estimation Program Interface Suite (EPI Suite™ Version 4.11, Stein, S. E. and Brown, R. L. 1994. *Estimation of normal boiling points from group contributions. J. Chem. Inf. Comput. Sci.* 34: 581-7.). Generally, to ensure low volatility according to EPI Suite™ Version 4.11, the calculated boiling point of compounds of Formula (I) or salts thereof may be at least 270° C. In various embodiments, the calculated boiling point of compounds of Formula (I) or salts thereof may be at least 270° C., at least 280° C., at least 290° C., or over 300° C.

In order for compounds of Formula (I) or salts thereof to be effective as an arthropod deterrent, these compounds must exhibit a high potency ($EC_{50}$ or $ED_{50}$) and high affinity ($K_i$ or $K_D$). Potency and affinity are measurements of the functional effect of the compound acting on the receptor. Affinity is the measurement of the strength of binding of the compound to the receptor. The potency and affinity refers to the concentration of the compound which induces a response halfway between the baseline and the maximum after a specified exposure time.

Generally, the compounds of Formula (II) or salt thereof may have potency ($EC_{50}$) of less than 1 μM. In various embodiments, the compounds of Formula (II) or salt thereof may have a potency of less than 1 μM, less than 100 nM, or less than 10 nM.

(VII) Compositions Comprising Compounds of Formula (II) or Salts Thereof.

Another aspect of the present disclosure encompasses compositions comprising Formula (II) or salts thereof and at least one additional component wherein the additional components are selected from a group comprising fragrances, solvents, propellants, diluents, surfactants, thickeners, coatings, paints, or combinations thereof. Collectively, the additional components comprise the "carrier." Additionally, these compositions may further comprise at least one known arthropod deterrent providing an enhanced arthropod deterrent mixture. These compositions may be further formulated into a form which may be easily applied to an article or a subject.

(a) Compounds of Formula (II) or Salts Thereof

The compounds of Formula (II) or salts thereof are described in Section V. In general, the composition comprising a compound of Formula (II) or a salt thereof contains the deterrent in an effective concentration.

The term "effective amount" describes an amount of deterrent present in a composition sufficient to produce a noticeable effect, such as a decreased frequency of mosquito bites. The effective amount can and will vary depending on many factors such as the arthropod or marine organism being deterred, severity of the infestation; individual subject parameters including age, physical condition, size and weight; concurrent treatments; area of treatments on the subject; the frequency of treatment; or the mode of administration. These factors are well known to those of ordinary skill in the art.

Generally, the concentration of the compound comprising Formula (II) or a salt thereof may range from about 0.0001% to 100% (w/w) of the total composition. In various embodiments, the concentration of the compound comprising Formula (II) or a salt thereof may range from about 0.0001% to 100%, from about 0.01% to about 75%, from about 0.1° A to 50%, or from 1° A to about 10% (w/w) of the total composition.

(b) Additional Components or "Carrier"

Depending on the final formulation used for the compositions comprising compounds of Formula (II) or a salt thereof, at least one additional component or carrier may be utilized in the composition. Additional components or "carriers" are described in more detail in Section (11)(b).

(c) Optional Known Deterrents

The composition, as described above, may further comprise an effective amount of an optional known deterrent. As discussed above, the "effective amount" of the optional known deterrent can and will vary as described previously. The optional known deterrents are described in more detail in Section (II)(c).

(d) Formulations

The compositions comprising compounds of Formula (II) or a salt thereof may be used in various forms for administration. These compositions are described in more detail in Section II.

(VIII) Method for Deterring Marine Biofouling Organisms using Compositions Comprising the Compounds of Formula (II) or Salts Thereof In still another aspect of the present disclosure encompasses methods for deterring aquatic and marine biofouling organisms. The method comprises providing a deterrent composition comprising the compounds of Formula (II) or salt thereof, coating a surface of an article thus providing an effective concentration of the deterrent on the article, and curing the composition. Examples of articles, aquatic and marine organisms, and the method are disclosed above in Section III.

(IX) Method for Deterring Terrestrial Arthropods using Compositions Comprising the Compounds of Formula (II) or Salt Thereof In yet another aspect of the present disclosure encompasses methods of deterring terrestrial arthropods. The method comprises providing a composition comprising the compounds of Formula (II) or salt thereof and applying the compositions to a surface of a subject thus providing an effective concentration of the arthropod deterrent on the subject. Terrestrial arthropods, suitable subjects, and methods of application are disclosed above in Section IV.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The compounds described herein have asymmetric centers. Compounds of the present disclosure containing an asymmetrically substituted atom may be isolated in optically active or racemic form. All chiral, diastereomeric, racemic forms and all geometric isomeric forms of a structure are intended, unless the specific stereochemistry or isomeric form is specifically indicated.

The term "acyl," as used herein alone or as part of another group, denotes the moiety formed by removal of the hydroxyl group from the group COOH of an organic carboxylic acid, e.g., RC(O)—, wherein R is R1, R1O—, R1R2N—, or R1S—, R1 is hydrocarbyl, heterosubstituted hydrocarbyl, or heterocyclo, and R2 is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "alkyl" as used herein describes groups which are preferably lower alkyl containing from one to eight carbon atoms in the principal chain and up to 20 carbon atoms. They may be straight or branched chain or cyclic and include methyl, ethyl, propyl, isopropyl, butyl, hexyl and the like.

The term "alkenyl" as used herein describes groups which are preferably lower alkenyl containing from two to eight carbon atoms in the principal chain and up to 20 carbon atoms. They may be straight or branched chain or cyclic and include ethenyl, propenyl, isopropenyl, butenyl, isobutenyl, hexenyl, and the like.

The term "alkynyl" as used herein describes groups which are preferably lower alkynyl containing from two to eight carbon atoms in the principal chain and up to 20 carbon atoms. They may be straight or branched chain and include ethynyl, propynyl, butynyl, isobutynyl, hexynyl, and the like.

The term "aromatic" as used herein alone or as part of another group denotes optionally substituted homo- or heterocyclic conjugated planar ring or ring system comprising delocalized electrons. These aromatic groups are preferably monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups, preferably monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon, with preferably 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring, and preferably 5 or 6 atoms in each ring. The heteroaromatic group preferably has 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring, and preferably 5 or 6 atoms in each ring. The heterocyclo group preferably has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties preferably comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

Having described the invention in detail, it will be apparent that modifications and variations are possible without departing from the scope of the invention defined in the appended claims.

EXAMPLES

The following examples illustrate various embodiments of the invention.

Example 1

Octopamine Receptors are an Underused Target for Repellants

Several arthropods had octopamine receptors (OctR) with pharmacological profiles consistent with an α-like OctR. *Periplaneta* (cockroach), *Ixodes* (tick), *Anopheles* (mosquito) isoform A, and *Aedes* (mosquito) OctRs each had an agonist profile consistent with an α-like OctR based on the higher potency and efficacy of octopamine over tryramine, and the stronger affinity for chlorpromazine compared to metoclopramide.

Commercial insect repellents do not interact strongly with the α-like OctRs. Referring to FIGS. 1A-D, the change in intercellular calcium concertation at the OctRs for *Drosophila* (FIG. 1A), *Aedes* (FIG. 1B), *Ixodes* (FIG. 1C), and *Periplanta* (FIG. 1D) were measured at a very high 100 μM concentrations of the widely used insect repellants paramenthane-3,8-diol (PMD), N,N-diethyl-meta-toluamide (DEET), 1-(1-methylpropoxycarbonyl)-2-(2-hydroxyethyl) piperidine (picaridin), and ethyl butylacetylaminopropionate (IR3535). Responses were normalized to the response with the endogenous agonist octopamine at a supersaturating concentration. PMD had the greatest response, reaching about 25% of the maximal response relative to octopamine in ticks, but registered less in the other species tested. The other repellants showed even poorer results. Therefore, commercial repellents have little or no effect on OctR even when tested at very high concentration.

Example 2

Several Compounds are Selective for Arthropod Species

Figure 2:
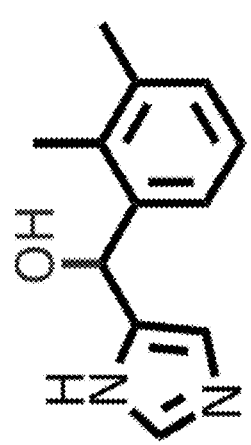
FIG. 2 shows the potency ($EC_{50}$) of AZ0024 tested against the octopamine receptors from *Balanus* (BiOctR), *Drosophila* (DmOctR), *Periplaneta* (PaOctR), *Aedes* (AeOctR), *Anopheles* Form A (AgAOctR) and *Ixodes* (IsTOctR). AZ0024 is highly selective for the AgAOctR over *Homo sapien* $α_2$-AR subtypes.
Figure 4:
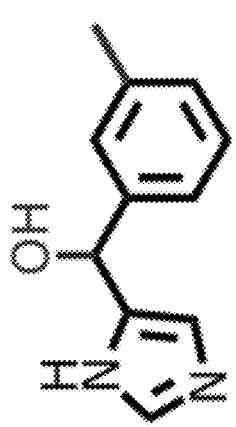
FIG. 4 shows the potency of AZ1410 tested against the octopamine receptors for *Anopheles* Form A (AgAOctR) and *Ixodes* (IsTOctR). AZ1410 is highly selective for the AgAOctR over *Homo sapien* $α_2$-AR subtypes.

AZ0024 (FIG. 2), AZ1399 (FIG. 3), AZ1410 (FIG. 4), and AZ1400 (FIG. 5) are selective for the *Anopheles gambiae* mosquito isoform A OctR. Selectivity was defined as the ratio of the affinity of compounds for the α2-AR subtypes over the potency of compounds for the different OctRs: Ki(Hsα2-AR)/EC 50(OctR). Thus selectivity is a measure of the fold-change or fold-difference between the concentration of compound that produces half the maximal signal at one receptor over that at the other, with larger fold-differences corresponding to a larger selectivity window. The larger the selectivity window the easier it is to produce a large response at the target arthropod OctRs while producing little or no response at the off-target vertebrate α2-ARs.

Functional expression of cloned arthropod OctRs and human α2-ARs: The cDNAs for α-like OctRs from different arthropod species (e.g., *Anopheles gambiae, Aedes aegypti, Periplaneta americana, Drosophila melanogaster, Ixodes scapularis, Balanus improvises*) and for α2-AR subtypes from humans were individually subcloned into mammalian expression vectors. These plasmids, which harbor a resistance gene for the selection drug G418 and the cDNA sequence for the receptor of interest, were individually transfected into mammalian cells using a calcium phosphate precipitation method. G418 selection was then employed to generated stable clonal cell lines. Utilizing rapid filtration radioligand binding techniques, the cell surface density of receptor expression of the individual clonal cell lines was determined at equilibrium and those with similar high levels of expression were selected for further experiments. Briefly, binding conditions were 50 mM Tris binding buffer pH 7.4 at 25° C. and an ice-cold wash buffer 10 mM Tris-HCl, pH 7.4). The radioligand was [3H]rauwolscine and non-specific binding was determined in the presence of 10 μM atipamezole. Following the addition of membranes prepared from the clonal cell lines, samples were mixed and allowed 2 hr. to reach equilibrium before rapid filtration and washing through 0.3% PEI-treated GF/C filters. The radioactivity remaining on the filters was quantified by scintillation counting. Receptor density (Bmax) was back calculated knowing the specific activity of the radioligand and applying the equation for a square hyperbola model: Bmax=(Y·(KD+X))/X, where Y is [specifically bound radioligand] and X=[radio ligand concentration]. The affinity (KD) for the radioligand for each receptor was determined in separate saturation isotherm binding experiments using the same binding conditions as describe above.

Measurement of compound affinities by competition radioligand binding: Affinities (Ki) for compounds were determined by [3H]rauwolscine competition binding using the same binding conditions as described above. The Ki values were calculated from $IC_{50}$ values using the Cheng-Prusoff equation.

Measurement of OctR activation by measuring changes in intracellular calcium: Activation of arthropod α-like OctRs increases intracellular calcium via a Gq-coupling mechanism. This involves activation of phospholipase C leading to an increase in intracellular inositol triphosphate (IP3) which then activates IP3-gated calcium channels in the endoplasmic reticulum causing a transient rise in intracellular calcium. These changes in intracellular calcium upon OctR activation were measured by loading cells with intracellular calcium sensitive dye CALCIUM 6QR and reading the change in calcium-induced fluorescent signal over time on a FlexStation 3 microplate reader.

Measurement of intracellular cyclic adenosine monophosphate (cAMP): Activation of human α2-ARs leads to an increase in intracellular cAMP via a Gs-coupling mechanism that involves activation of adenylyl cyclase. The changes in intracellular cAMP were measured by incubating cell lysates with the cAMP-Glo reagent and reading changes in chemilumenescence on a microplate reader.

AZ0027 is a low volatility OctR activator which protects against *Aedes* mosquito biting and is selective for *Anopheles* mosquito, *Ixodes* tick, and *Periplaneta* cockroach OctRs. FIG. 6. AZ0027 is over 500-fold more potent than DEET and is non-toxic to mosquitoes. For DEET the lowest concentration that produces maximal protection against mosquito biting is lethal in half the mosquitoes (i.e., $LC_{50}$). This level of toxicity affects fitness and thereby provides a selective pressure for encouraging resistance to DEET. AZ0027, on the other hand, is effective at levels far below the lethal dosage for mosquitoes and would not have the unwanted side effect of producing mosquitoes that are resistant to AZ0027.

Figure 7:
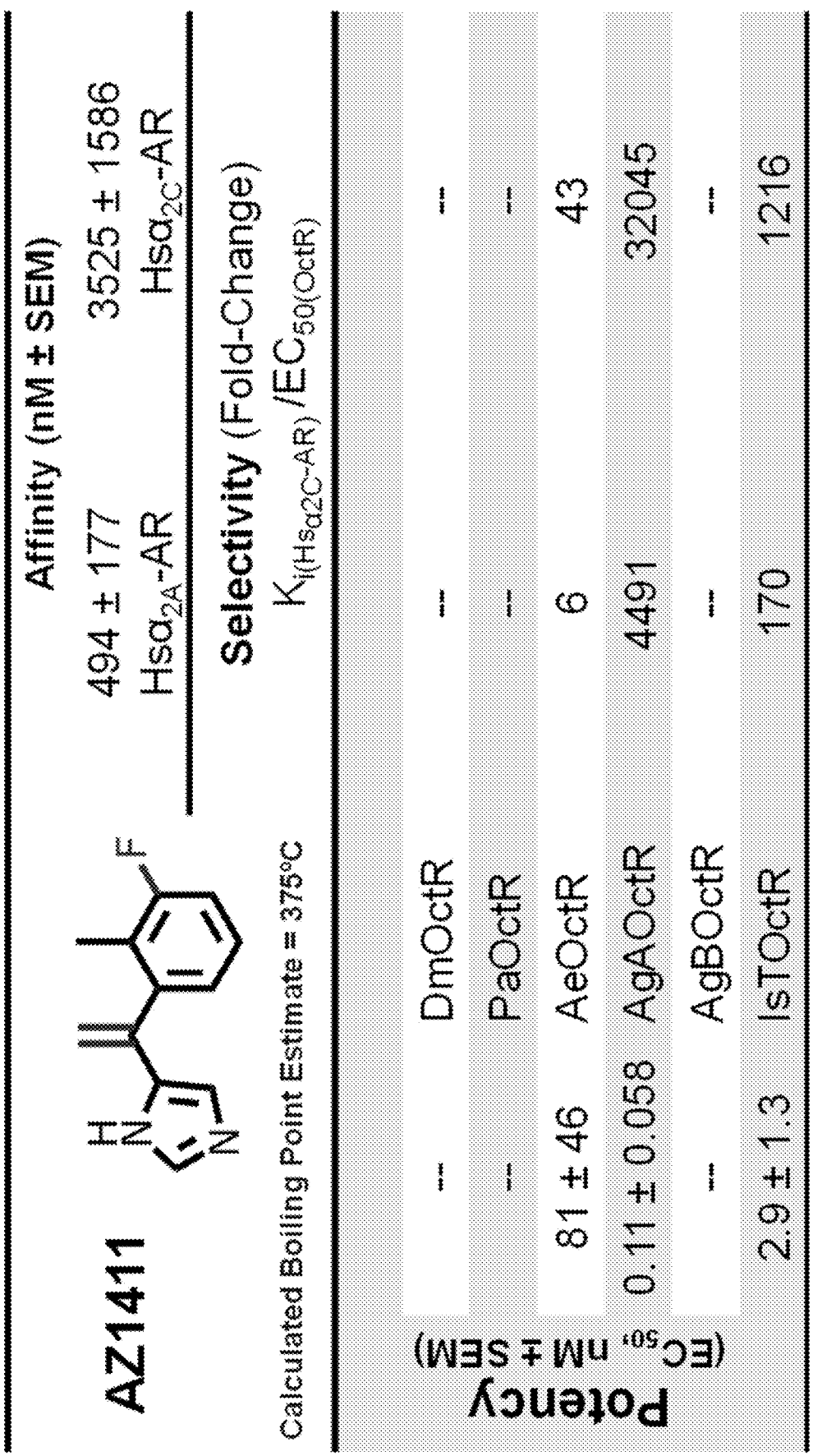
FIG. 7 shows the potency of AZ1411 tested against the octopamine receptors from *Periplaneta* (PaOctR), *Aedes* (AeOctR), *Anopheles* Form A (AgAOctR) and *Ixodes* (IsTOctR). AZ1411 is highly selective for the *Anopheles* mosquito isoform A and *Ixodes* tick OctRs over *Homo sapien* $α_2$-AR subtypes.
Figure 8:
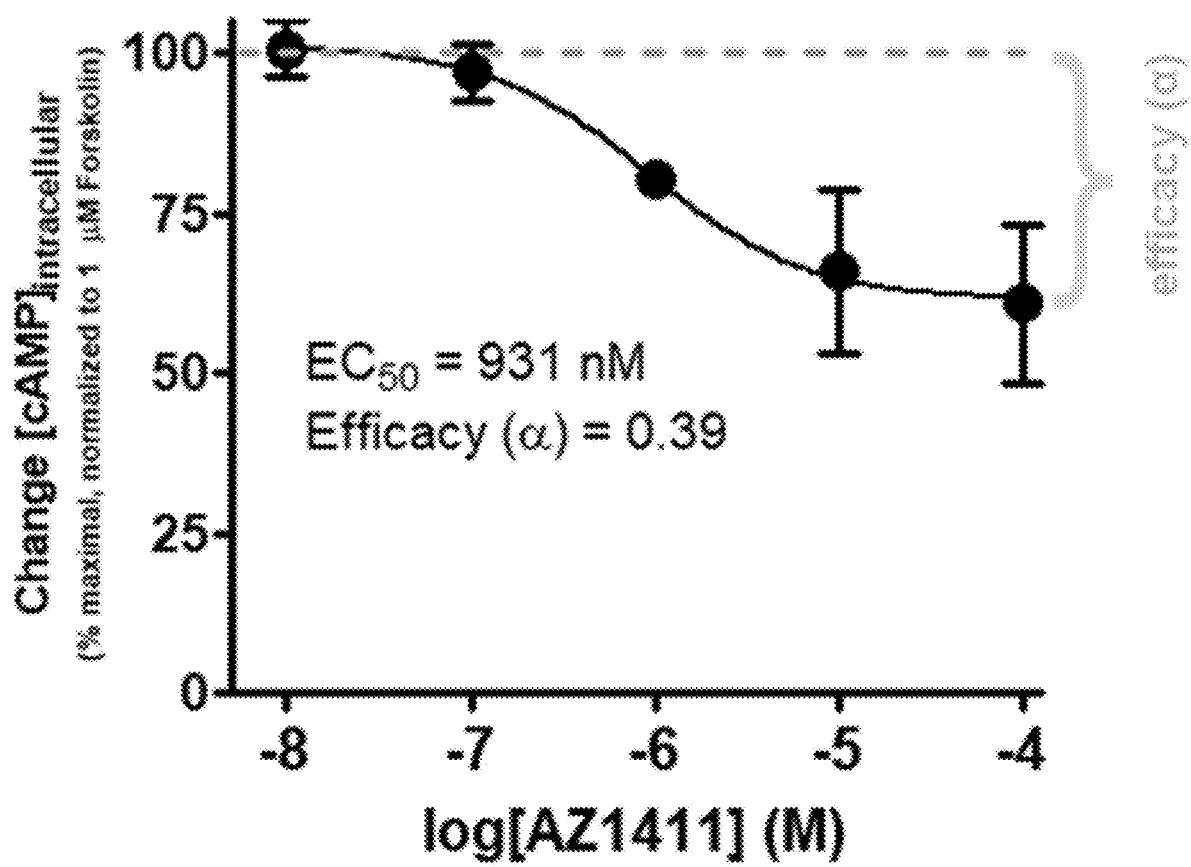
FIG. 8 shows the change in intracellular cyclic AMP concentration, with the maximal percentage normalized to 1 µM forskolin as a function of the log of AZ1411 concentration in moles per liter (M). AZ1411 acts as a low potency, partial agonist of the human $α_{2c}$ adrenergic receptor ($α_{2c}$-AR).

AZ1411 is selective for the *Anopheles gambiae* mosquito isoform A and *Ixodes scapularis* tick OctRs. FIG. 7. AZ1411 acts as a low potency, partial agonist of the human α2C adrenergic receptor. FIG. 8. AZ1411's functional profile at the α2C adrenergic receptor indicates a low potential for off-target effects in humans.

Figure 9:
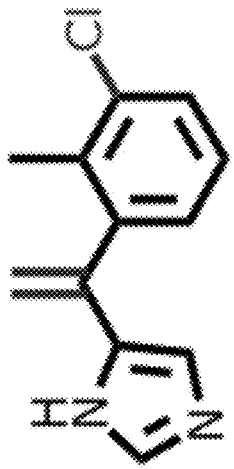
FIG. 9 shows the potency of AZ1436 tested against the octopamine receptors for *Periplaneta* (PaOctR), *Anopheles* Form A (AgOctR) and *Ixodes* (IsTOctR). AZ1436 is highly selective for the *Anopheles* mosquito isoform AOctR over *Homo sapien* $α_2$-AR subtypes.

AZ1436 is a potent full agonist at *Anopheles gambiae* mosquito isoform A and *Ixodes scapularis* tick OctRs. FIG. 9. AZ1436 has 2-4 high potency for OctRs than is fluorinated AZ1411. Preliminary studies suggest it is likely an antagonist at α2-ARs. AZ1436's functional profile at the α2C-AR indicated a low potential for off-target effects in humans.

Figure 10:
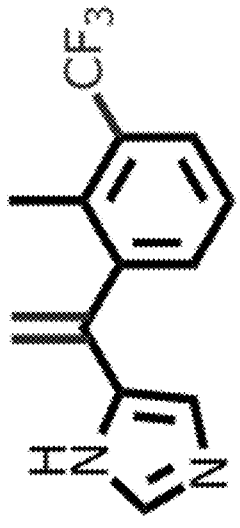
FIG. 10 shows the potency of AZ1415 tested against the octopamine receptors for *Anopheles* Form A (AgOctR) and *Ixodes* (IsTOctR). AZ1415 is highly selective for the *Anopheles* mosquito isoform A OctRs.

AZ1415 has high potency and full efficacy for *Anopheles gambiae* mosquito isoform A OctRs. FIG. 10.

The E-isomer of the ethylene-substituted compound (AZ1440) has higher potency than the Z-isomer (AZ1409), though for the tick OctR efficacy is lost. FIG. 11. The bridge substitution had a stereoselective effect, just like between the enantiomers of medetomidine.

Bridge keto analogues of octopamine (CN19745) and medetomidine (AK128046) have moderate potency at *Anopheles* OctR, but good selectivity over α2C-AR. FIG. 12. The affinity ($K_i$) for AK128046 at the human αa2C adrenergic receptor was 10,590 nM.

While specific embodiments have been described above with reference to the disclosed embodiments and examples, such embodiments are only illustrative and do not limit the scope of the disclosure. Changes and modifications can be made in accordance with ordinary skill in the art without departing from the disclosure in its broader aspects as defined in the following claims.

Example 3

Mosquito Repellent Bioassay (Simulated Field Study)

The mosquito repellent bioassays used repellency chambers were produced by Sierra Research Laboratories. The repellency evaluations were conducted in two plastic containers (10" wide×16" long×12" high) connected at the ends with a 2.5" Plexiglas "T" tube. The Plexiglas tube measures 16" long with a "T" connection at the mid-point of the Plexiglas tube. The "T" portion was 2" in diameter and 8" long plugged with a rubber stopper. The plastic containers are clear, with a lid and a cut out portion, opposite the "T" end. The cut-out portion was covered with elastic cotton sock for access. Each container was labeled as a treatment group (A) and a control group (B). Filter paper (104 in$^2$) was placed at the bottom of each container and a screw eye was placed in the center of the container lids to suspend the mouse tube cage.

Each replicate (mouse) was sprayed with approximately 1 to 2 mL of the test substance and allowed to dry. The untreated mice were placed within ¼" hardwire cloth tube (approximately 1" in diameter with snap cap ends) and hung by a wire from the repellency chamber lids, A caged mouse was placed on each side of the repellency chamber (treated side and control side). The mosquitos were evaluated for feeding activity and aggressiveness prior to being aspirated from their rearing cages and released into the test system. Mosquito landing (LIB: landing with intent to bite) and biting (biting and feeding :visual) counts were conducted simultaneously for one minute on each of the repellency chamber at 15, 30, and 45 minutes after introduction of the mice. Final mosquito counts were made by aspirating the mosquitos out of the test system at one-hour post introduction of the mice. Mosquitos remaining in the center tube portion of the test system were not included in the total mosquito counts. Five replicated were evaluated. The tables below show the results of the Arthropod deterrents versus DEET.

| Treatment Group: J-0027 (2.5%) on Mouse over Sod Anthropod Species: Yellow Fever Mosquito-*Aedes aegypti* | | | | |
|---|---|---|---|---|
| | # of LIB Treated- 1 Minute Observation | | | |
| Replicate # | 5 min. | 30 min. | 60 min. | Total |
| 1 | 11 | 9 | 6 | 26 |
| 2 | 16 | 8 | 9 | 33 |
| 3 | 11 | 14 | 8 | 33 |
| 4 | 0 | 1 | 2 | 3 |
| 5 | 7 | 4 | 6 | 17 |
| Σ | 45 | 36 | 31 | 112 |
| % Repel | 41.6 | 59.1 | 70.2 | 58.2 |
| 1 | 37 | 39 | 41 | 117 |
| 2 | 24 | 25 | 26 | 75 |
| 3 | 3 | 5 | 6 | 14 |
| 4 | 3 | 12 | 21 | 36 |
| 5 | 10 | 7 | 10 | 27 |
| Σ | 77 | 88 | 104 | 269 |

| Treatment Group: OFF 15% DEET on Mouse over Sod Anthropod Species: Yellow Fever Mosquito-*Aedes aegypti* | | | | |
|---|---|---|---|---|
| | # of LIB Treated- 1 Minute Observation | | | |
| Replicate # | 5 min. | 30 min. | 60 min. | Total |
| 1 | 0 | 0 | 0 | 0 |
| 2 | 0 | 0 | 0 | 0 |
| 3 | 0 | 0 | 0 | 0 |
| 4 | 0 | 0 | 0 | 0 |
| 5 | 0 | 0 | 0 | 0 |
| Σ | 0 | 0 | 0 | 0 |
| % Repel | 100 | 100 | 100 | 100 |
| 1 | 10 | 17 | 22 | 49 |
| 2 | 3 | 7 | 17 | 27 |
| 3 | 12 | 13 | 7 | 32 |
| 4 | 11 | 6 | 8 | 25 |
| 5 | 13 | 15 | 18 | 46 |
| Σ | 49 | 58 | 72 | 179 |

Example 4

Process for Preparing the Compounds Comprising Formula (V)

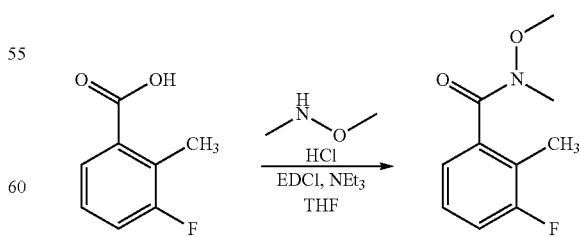

Into a round bottom flask may be added the substituted benzoic acid (1.0 mmol), N,O-dimethylhydroxylamine hydrochloride (1.25 mmol), triethylamine (1.3 mmol), and dry tetrahydrofuran (20 mL) at room temperature under a nitrogen atmosphere. After stirring was initiated, N-(3-dimethylaminopropyl)-N'-ethylcarbodiimide hydrochloride (1.25 mmol) and triethylamine (1.3 mmol) were added. The reaction may be stirred at room temperature for 24 h until deemed complete by TLC. At that time, the solvent may be removed under reduced pressure. To the residue may be added distilled water (15 mL). After stirring for 15 minutes, the mixture may be extracted with ethyl acetate (3×20 mL) and the organic extracts may be combined, may be washed with dilute 1.0 M HCl (2×10 mL), distilled water (2×10 mL), saturated brine (10 mL), the ethyl acetate layer may be dried over anhydrous Na$_2$SO$_4$, filtered, and evaporated. The product (Weinreb Amide) may be isolated using column chromatography.

Example 5

Process for Preparing the Compounds Comprising Formula (Ia)

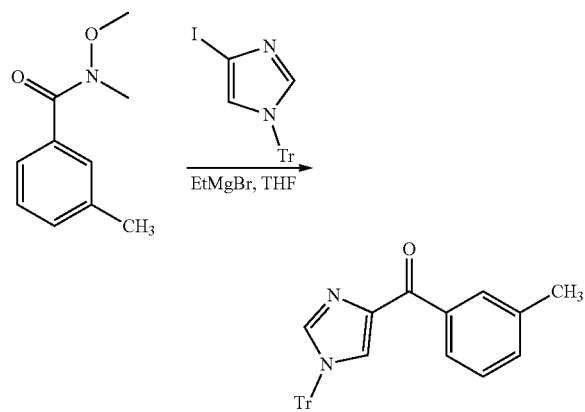

Tr = triphenylmethyl

Into a round bottom flask may be added the benzamide (1.0 mmol), 4-iodo-1-(triphenylmethyl)-1H-imidazole (1.2 mmol), and dry tetrahydrofuran (20 mL) at room temperature under a nitrogen atmosphere. The reaction may be cooled to 0° C. and then EtMgBr (1.5 mmol, 1.0M in THF) may be added dropwise. The reaction mixture was allowed to stir until deemed complete (TLC, HPLC). Then, a saturated solution of NH$_4$Cl may be added dropwise, and may be stirred for 30 minutes. The pH of the mixture may be adjusted to pH 12 using 10% aqueous NaOH. The mixture may be extracted using ethyl acetate (3×20 mL), the extracts combined, and dried over anhydrous Na$_2$SO$_4$. The product may be isolated using column chromatography.

Example 6

Process for Preparing the Compounds Comprising Formula (Ib)

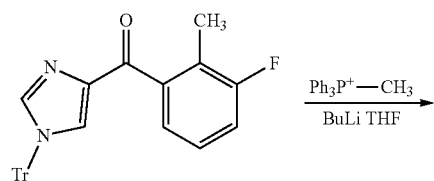

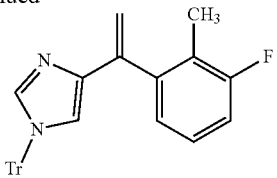

Tr = triphenylmethyl

Into a 3 necked round bottom flask equipped with a reflux condenser, an addition funnel, and a gas inlet tube may be added 25 mL anhydrous Et$_2$O and n-butyl lithium (1.05 mmol in anhydrous Et$_2$O). The flask may be cooled to 0° C. and methyltriphenylphosphonium bromide (1.05 mmol) may be cautiously added over a 30 minute period. The reaction may be warmed to room temperature and may be stirred for 6 hours. Then, a solution of the ketoimidazole (1.05 mmol) in a solution of 25 mL anhydrous Et$_2$O may be added dropwise. After the addition was complete, the reaction may be refluxed overnight, may be allowed to cool to room temperature, and the precipitate may be removed by vacuum filtration. The precipitate may be washed with 25 mL of ether. The combined ethereal filtrates may be washed with distilled water (3×10 mL) and saturated brine (10 mL). The ether filtrates may be dried over anhydrous Na$_2$SO$_4$, may be filtered, and the ether may be removed under vacuum. The product may be isolated by column chromatography.

Example 7

Process for Preparing the Compounds Comprising Formula (Ib)

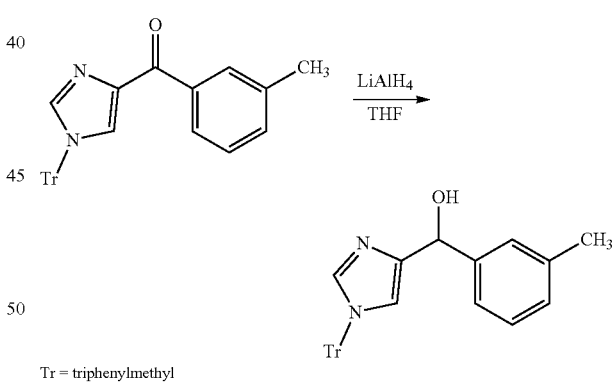

Tr = triphenylmethyl

Into a round bottom flask may be added the keto imidazole (1.0 mmol) and anhydrous THF (25 mL). The flask may be cooled to 0° C. and LiAlH$_4$ (0.5 mmol) may be added in portions over a 30 minutes period. The reaction mixture may be stirred at room temperature for 6 h at room temperature when the reaction may be deemed complete. Then, distilled water (10 mL) may be added and the reaction mixture may be extracted with EtOAc (3×20 mL). The extracts may be combined, may be washed with saturated brine (10 mL), may be dried over anhydrous Na$_2$SO$_4$, may be filtered, and may be concentrated. The product may be isolated by column chromatography.

Example 8

Process for Preparing the Compounds Comprising Formula (Ib)

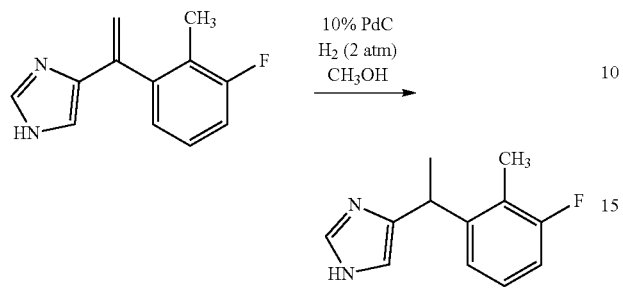

Into a Parr Bottle may be added the imidazole (1.0 mmol), 10% Pd—C (25 mg), and methanol (25 mL). The Parr bottle may be attached to a Parr Shaker and may be degassed 5 times with nitrogen. Then, hydrogen may be introduced into the Parr bottle to 2.0 atmospheres. The reaction may be shaken for a period of 6 h while periodically adding hydrogen gas to maintain the pressure at 2.0 atmospheres. At that time, the reaction may be deemed complete. The pressure with the Parr bottle may be released and may be replaced with nitrogen. The Parr bottle may be removed from the Parr Shaker and the solution may be filtered through a celite pad and the pad may be washed with methanol (10 mL). The methanol may be removed under vacuum and the product may be isolated by column chromatography.

Example 9

Process for Preparing the Compounds Comprising Formula (Ib)

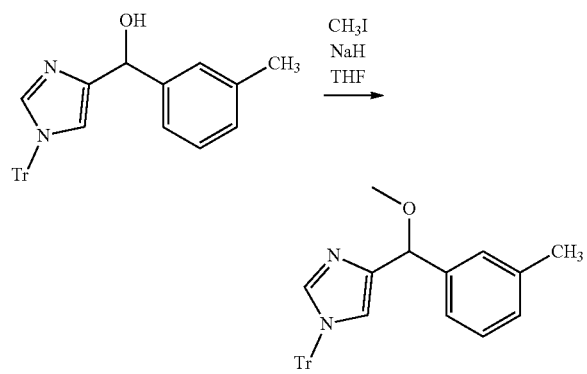

Tr = triphenylmethyl

Into a round bottom flask was added the alcohol (1.0 mmol) in THF (20 mL). To this solution may be added NaH (1.0 mmol) and the reaction may be stirred at room temperature for 1 h. Then, methyl iodide (1.0 mmol) may be added. The reaction may be stirred at room temperature overnight when the reaction may be deemed complete. Then, water may be added and the mixture may be extracted using EtOAc (3×20 mL). The extracts may be combined, may be washed with saturated brine (10 mL), dried over anhydrous $Na_2SO_4$, filtered, and the solvent removed under vacuum. The product may be isolated by column chromatography.

What is claimed is:

1. An arthropod deterrent composition comprising:
   a) at least one of an effective amount of the arthropod deterrent of the compound of Formula (I) or a salt thereof;

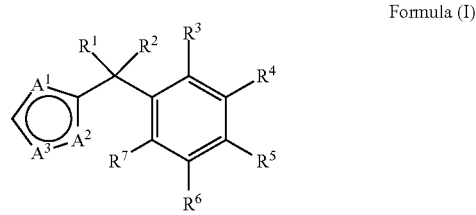

Formula (I)

b) at least one additional component selected from a group comprising fragrances, solvents, diluents, fixatives, carrier, paints, coatings, or combinations thereof; wherein $A^1$, $A^2$, and $A^3$ is independently selected from a group consisting of carbon, nitrogen, oxygen, and sulfur;
   $R^1$ and $R^2$ are independently selected from a group consisting of hydrogen, deuterium, hydroxyl, $C_1$-$C_6$ substituted or unsubstituted alkyl, $C_2$-$C_6$ substituted or unsubstituted alkenyl, $C_1$-$C_6$ substituted or unsubstituted alkoxy; or $R^1$ and $R^2$ may be taken together to form a $C_1$-$C_6$ substituted or unsubstituted alkenyl, or =O; and
   $R^3$, $R^4$, $R^5$, $R^6$, and $R^7$ are independently selected from a group consisting of hydrogen, deuterium, halogen, hydroxyl, $C_1$-$C_6$ substituted or unsubstituted alkoxy, $C_1$-$C_6$ substituted or unsubstituted alkyl, $R^1$ and $R^3$ may be taken together to form a $C_1$-$C_6$ substituted or unsubstituted cycloalkyl, or $C_2$-$C_6$ substituted or unsubstituted cycloalkenyl, $R^2$ and $R^3$ may be taken together to form a $C_1$-$C_6$ substituted or unsubstituted cycloalkyl, or $C_2$-$C_6$ substituted or unsubstituted cycloalkenyl, or $R^3$ and $R^4$ may be taken together to form a $C_1$-$C_5$ substituted or unsubstituted cycloalkyl, $C_2$-$C_6$ substituted or unsubstituted cycloalkenyl, or substituted or unsubstituted aryl.

2. The composition of claim 1, wherein $A^1$ is nitrogen, and $A^2$ and $A^3$ are carbon.

3. The composition of claim 1, wherein $A^3$ is nitrogen, and $A^1$ and $A^2$ are carbon.

4. The composition of claim 1, wherein $A^1$ and $A^2$ are nitrogen, and $A^3$ is carbon.

5. The composition of claim 1, wherein $A^1$ and $A^3$ are nitrogen, and $A^2$ is carbon.

6. The composition of claim 1, wherein $A^1$, $A^2$, and $A^3$ are nitrogen.

7. The composition of claim 1, wherein $R^1$ and $R^2$ are independently selected from a group consisting of hydrogen, deuterium, hydroxyl, $C_1$-$C_4$ substituted or unsubstituted alkyl, $C_2$-$C_4$ substituted or unsubstituted alkenyl, $C_1$-$C_4$ substituted or unsubstituted alkoxy; or $R^1$ and $R^2$ may be taken together to form a $C_2$-$C_4$ substituted or unsubstituted alkenyl, or =O.

8. The composition of claim 7, wherein $R^1$ and $R^2$ are independently selected from a group consisting of hydrogen, methyl, ethyl, propyl, isopropyl, methoxy, ethoxy, propoxy, isopropoxy, hydroxyl, —$CH_2CH$=$CH_2$, —$CH_2C(CH_3)$ =CH$_2$, —CH=C(CH$_3$)$_2$, —CH=CHCH$_3$; or R$^1$ and R$^2$ may be taken together to form =CH$_2$, =CHCH$_3$, =C(CH$_3$)$_2$, or =O.

9. The composition of claim 8, wherein each R$^1$ and R$^2$ are independently selected from a group consisting hydrogen, methyl, methoxy, hydroxyl, —CH$_2$CH=CH$_2$, —CH=CHCH$_3$; or R$^1$ and R$^2$ may taken together to form =CH$_2$, =CH—CH$_3$, or =O.

10. The composition of claim 1, wherein each R$^3$ and R$^4$ are independently selected from a group consisting of hydrogen, deuterium, halogen, C$_1$-C$_4$ substituted or unsubstituted alkyl, C$_1$-C$_4$ substituted or unsubstituted alkoxy, or R$^3$ and R$^4$ may be taken together to form a C$_1$-C$_5$ substituted or unsubstituted cycloalkyl, or substituted or unsubstituted aryl.

11. The composition of claim 10, wherein each R$^3$ and R$^4$ are independently selected from a group comprising hydrogen, deuterium, methyl, ethyl, propyl, isopropyl, fluoromethyl, difluoromethyl, trifluoromethyl, fluoroethyl, difluoroethyl, trifluoroethyl, tetrafluoroethyl, pentafluoroethyl, bromine, chlorine, or fluorine, or R$^3$ and R$^4$ may be taken together to form a cyclopropyl, cyclobutyl, cyclohexyl, cycloheptyl, cyclopentenyl, cyclohexenyl, or cycloheptenyl, or an aryl.

12. The composition of claim 11, wherein each R$^3$ and R$^4$ are independently selected from a group comprising hydrogen, deuterium, methyl, trifluoromethyl, chlorine, fluorine, R$^3$ and R$^4$ may be taken together to form aryl.

13. The compound of claim 1, wherein R$^1$ and R$^3$ may be taken together to form a C$_2$-C$_4$ substituted or unsubstituted cycloalkyl, or C$_2$-C$_4$ substituted or unsubstituted cycloalkenyl, or R$^2$ and R$^3$ may be taken together to form a C$_2$-C$_4$ substituted or unsubstituted cycloalkyl, or C$_2$-C$_4$ substituted or unsubstituted cycloalkenyl.

14. The compound of claim 13, wherein R$^1$ and R$^3$ may be taken together to form a cyclopropyl, cyclobutyl, cyclopentyl, cyclohexyl, cycloheptyl, cyclopentenyl, or cyclohexenyl, or R$^2$ and R$^3$ may be taken together to form a cyclopropyl, cyclobutyl, cyclopentyl, cyclohexyl, cycloheptyl, cyclopentenyl, or cyclohexenyl.

15. The compound of claim 14, wherein R$^1$ and R$^3$ may be taken together to form a cyclopentyl or cyclohexyl, or R$^2$ and R$^3$ may be taken together to form a cyclopentyl or cyclohexyl.

16. The composition of claim 1, wherein each R$^5$, R$^6$, and R$^7$ are independently selected from a group consisting of hydrogen, deuterium, halogen, C$_1$-C$_4$ substituted or unsubstituted alkyl, or C$_1$-C$_4$ substituted or unsubstituted alkoxy.

17. The composition of claim 16, wherein each R$^5$, R$^6$, and R$^7$ are independently selected from a group consisting of hydrogen, deuterium, methyl, ethyl, chlorine, or fluorine.

18. The composition of claim 17, wherein R$^5$, R$^6$, and R$^7$ are hydrogen or deuterium.

19. The composition of claim 1, wherein the compound is selected from a group comprising:

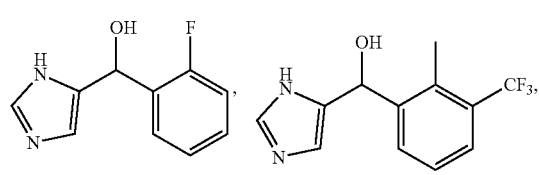

-continued

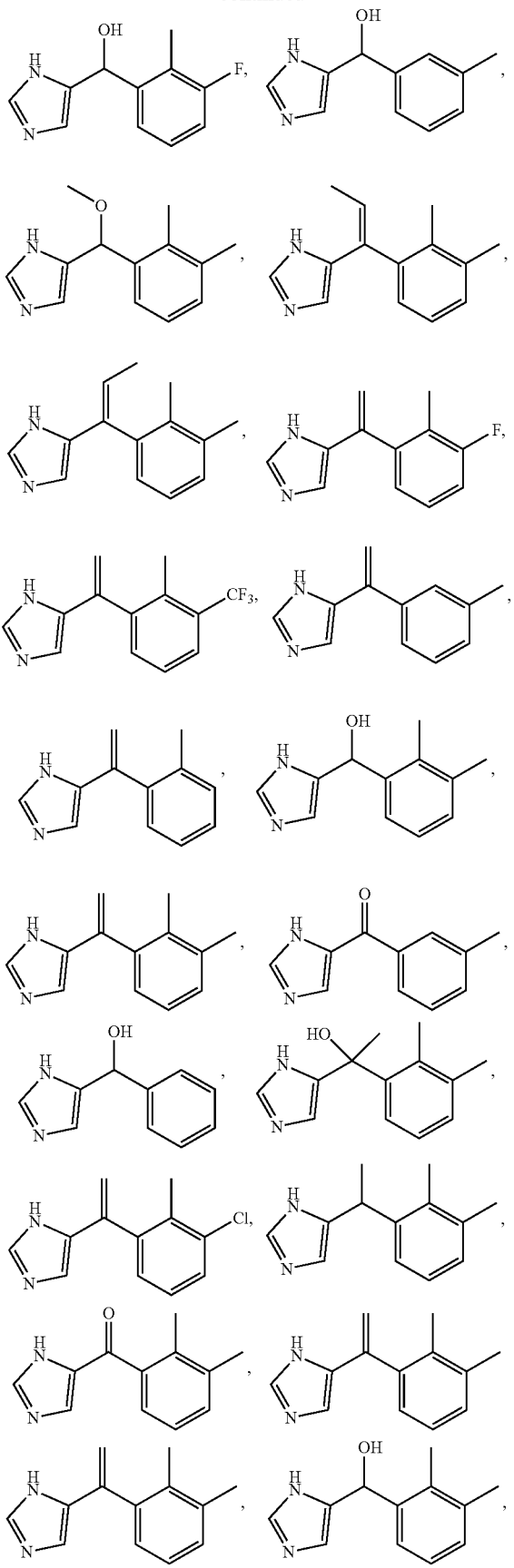

-continued

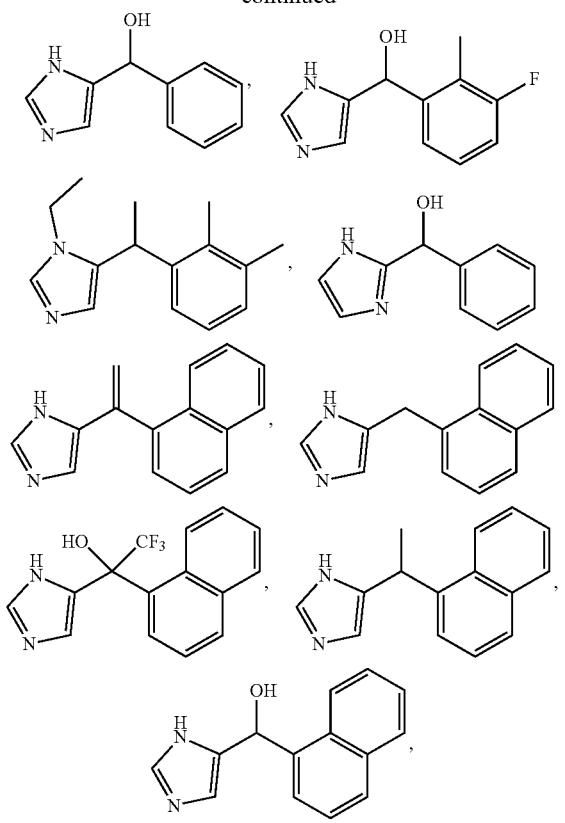

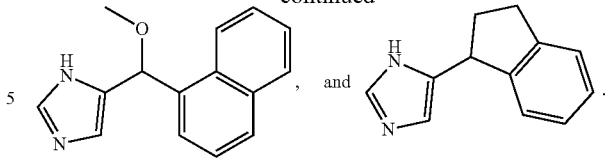

20. The composition of claim 1, arthropod deterrent of the compound of Formula (I) or a salt thereof ranges from about 0.0001% to 100% (w/w) of the total composition.

21. The composition of claim 1, wherein the composition further comprises at least one compound selected from a group comprising N,N-diethyl-meta-toluamide, 1-(1-methylpropoxycarbonyl)-2-(2-hydroxyethyl)piperidine, para-menthane-3,8-diol (PMD, active in Oil of Eucalytus), ethyl 3-[acetyl(butyl)amino]propanoate, (2S)-1-[(1S)-cyclohex-3-en-1-ylcarbonyl]-2-methylpiperidine, essential oils, etc. for terrestrial arthropods, and copper, zinc and other metals and their oxides, 3-(3,4-dichlorophenyl)-1,1-dimethylurea, 2-methylthio-4-tert-butylamino-6-cyclopropylamino-s-triazine), zincpyrothione (Zinc, Ms(I-hydroxy-2(IH)-pyridinethionato-O,S)-, (T-4)-), copper pyrothione (Copper, Ms(I-hydroxy-2(IH)-pyridinethionato-O,S)-, (T-4)-), diclofluanide (N'-dimethyl-N-phenylsulphamide), zinc ethylene bisdithiocarbamate, zinc bis(dimethylthiocarbamates)) (3-5), quaternary ammonium compounds, 4,5-dichloro-2-n-octyl-3(2H)-isothiazolone, 2-(p-chlorophenyl)-3-cyano-4-bromo-5-trifluoromethyl, or combinations thereof.

22. The composition of claim 1, wherein the composition is in the form of a spray, an aerosol, a gel, a cream, a lotion, a paint, or a coating.

\* \* \* \* \*